(12) United States Patent
Barth et al.

(10) Patent No.: US 6,995,184 B2
(45) Date of Patent: Feb. 7, 2006

(54) 3-ARYLINDOLE DERIVATIVES AND THEIR USE AS $CB_2$ RECEPTOR AGONISTS

(75) Inventors: Francis Barth, Saint-Georges d'Orques (FR); Christian Congy, Saint-Gely-du-Fesc (FR); Carole Guillaumont, Aigues-Vives (FR); Murielle Rinaldi, Saint-Georges d'Orques (FR); Fabienne Vasse, Montpellier (FR); Claude Vernhet, Montpellier (FR)

(73) Assignee: Sanofi-Aventis, Paris (FR)

( * ) Notice: Subject to any disclaimer, the term of this patent is extended or adjusted under 35 U.S.C. 154(b) by 340 days.

(21) Appl. No.: 10/416,617

(22) PCT Filed: Nov. 21, 2001

(86) PCT No.: PCT/FR01/03665

§ 371 (c)(1),
(2), (4) Date: May 30, 2002

(87) PCT Pub. No.: WO02/42269

PCT Pub. Date: May 3, 2000

(65) Prior Publication Data

US 2004/0034090 A1 Feb. 19, 2004

(30) Foreign Application Priority Data

Nov. 22, 2000 (FR) .................................. 00 15158

(51) Int. Cl.
*A61K 31/404* (2006.01)
*A61K 31/405* (2006.01)
*C07D 209/08* (2006.01)

(52) U.S. Cl. ...................... 514/419; 514/415; 548/469; 548/491

(58) Field of Classification Search ................ 514/415, 514/419; 548/469, 491
See application file for complete search history.

(56) References Cited

U.S. PATENT DOCUMENTS 5,532,237 A  7/1996 Gallant et al.
6,013,648 A * 1/2000 Rinaldi et al. ........... 514/235.2

FOREIGN PATENT DOCUMENTS

WO    WO 97/00860    * 1/1997  ............. 514/235.2
WO    WO 01/28557    4/2001

OTHER PUBLICATIONS

Eissenstat, et al. Aminoalkylindoles: Structure-Activity Relationships of Novel Cannabinoid Mimetics, J. Med. Chem. vo. 38, pp. 3094-3105 (1995).*

* cited by examiner

*Primary Examiner*—Taofiq Solola
*Assistant Examiner*—Nyeemah Grazier
(74) *Attorney, Agent, or Firm*—Balaram Gupta

(57) ABSTRACT

A subject-matter of the present invention is compounds of formula:

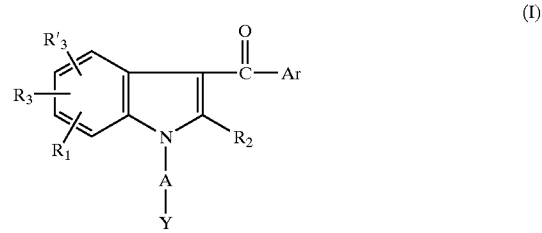

and their preparation and the pharmaceutical compositions comprising them. These compounds are agonists for $CB_2$ cannabinoid receptors.

30 Claims, No Drawings

3-ARYLINDOLE DERIVATIVES AND THEIR USE AS CB₂ RECEPTOR AGONISTS

A subject-matter of the present invention is novel compounds derived from 3-aroylindole, which are agonists of CB$_2$ cannabinoid receptors, their process of preparation and the pharmaceutical compositions comprising them.

Δ$^9$-THC is the main active constituent extracted from *Cannabis sativa* (Tuner, 1985; In Marijuana 1984, edited by Harvey, D Y, IRL Press, Oxford).

Numerous articles have described not only psychotropic effects of cannabinoids but also an influence of the latter on the immune function [HOLLISTER L. E., J. Psychoact. Drugs, 24 (1992), 159–164]. Most of the in vitro studies have shown immunosuppressant effects for cannabinoids: the inhibition of the proliferative responses in T lymphocytes and B lymphocytes induced by mitogens [Luo, Y. D. et al., Int. J. Immunopharmacol., (1992) 14, 49–56, Schwartz, H. et al., J. Neuroimmunol., (1994) 55, 107–115], the inhibition of the activity of cytotoxic T cells [Klein et al., J. Toxicol. Environ. Health, (1991) 32, 465–477], the inhibition of the microbiocidal activity of macrophages and of the synthesis of TNFα [Arata, S. et al., Life Sci., (1991) 49, 473–479; Fisher-Stenger et al., J. Pharm. Exp. Ther., (1993) 267, 1558–1565], the inhibition of the cytolytic activity and of the production of TNFα of large granular lymphocytes [Kusher et al., Cell. Immun., (1994) 154, 99–108]. In some studies, amplification effects were observed: increase in the bioactivity of interleukin-1 by mice resident macrophages or differentiated macrophage cell lines, due to increased levels of TNFα [Zhu et al., J. Pharm. Exp. Ther., (1994) 270, 1334–1339; Shivers, S. C. et al., Life Sci., (1994) 54, 1281–1289].

The effects of cannabinoids are due to interaction with specific high affinity receptors, coupled to G proteins, present at the central level (Devane et al., Molecular Pharmacology (1988), 34, 605–613) and the peripheral level (Nye et al., J. Pharmacol. and Exp. Ther. (1985), 234, 784–791; Kaminski et al., Molecular Pharmacol. (1992), 42, 736–742 ; Munro et al., Nature (1993), 365, 61–65).

The central effects of cannabinoids relate to a first type of cannabinoid receptor (CB$_1$) which is present mainly in the brain but also in the periphery. Furthermore, Munro et al. [Nature, (1993) 365, 61–65] have cloned a second type of cannabinoid receptor, CB$_2$, which is present in the periphery and more particularly on cells of immune origin. The presence of CB$_2$ cannabinoid receptors on lymphoid cells may explain the immunomodulation mentioned above exerted by agonists for cannabinoid receptors.

Certain indole derivatives have been mentioned in the prior art as exhibiting an affinity for CB$_2$ receptors. Thus, U.S. Pat. No. 5,532,237 discloses compounds of formula:

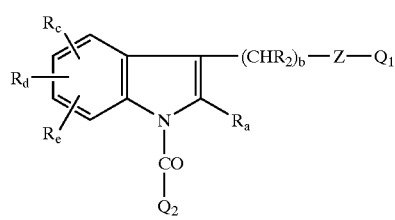

(A)

in which the substituents have various values;

and Patent Application EP 833 818 discloses compounds of formula:

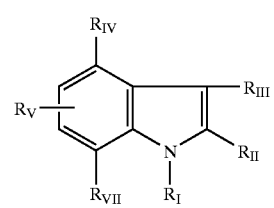

(B)

in which the substituents have various values.

A subject-matter of the present invention is compounds of formula:

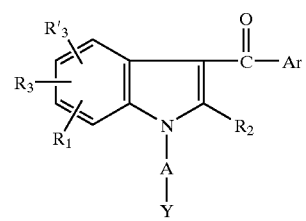

(I)

in which:
  Ar represents:
    a) a phenyl mono-, di- or trisubstituted by one or more groups chosen from: a halogen atom, a (C$_1$–C$_4$)alkyl, a trifluoromethyl, an amino, a nitro, a hydroxyl, a (C$_1$–C$_4$)alkoxy, a (C$_1$–C$_4$)alkylsulphanyl or a (C$_1$–C$_4$)alkylsulphonyl;
    b) a naphthyl which is unsubstituted or substituted once or twice by a halogen atom, a (C$_1$–C$_4$)alkyl or a trifluoromethyl;
  A represents a C$_2$–C$_6$ alkylene radical;
  Y represents a group chosen from SR$_4$, SOR$_4$, SO$_2$R$_4$, SO$_2$NR$_5$R$_6$, N(R$_7$)SO$_2$R$_4$, OR$_4$ or NR$_7$SO$_2$NR$_5$R$_6$;
  R$_1$, R$_3$ and R'$_3$ represent, each independently of one another, hydrogen, a hydroxyl, a halogen atom, a (C$_1$–C$_4$)alkyl, a trifluoromethyl or a (C$_1$–C$_4$)alkoxy;
  R$_2$ represents hydrogen or a (C$_1$–C$_4$)alkyl;
  R$_4$ represents a (C$_1$–C$_4$)alkyl or a trifluoromethyl
  R$_5$ and R$_6$ each independently represent hydrogen or a (C$_1$–C$_4$)alkyl;
  R$_7$ represents hydrogen or a (C$_1$–C$_4$)alkyl and their optional salts and their solvates.

The term "halogen" is understood to mean a chlorine, bromine, fluorine or iodine atom.

The term "alkyl" or "alkylidene" is understood to mean a linear or branched radical.

When the compounds of formula (I) comprise an asymmetric sulphur atom or asymmetric carbon atom, all the optical isomers and their mixture in any proportions are subject-matters of the invention.

The salts are generally prepared with pharmaceutically acceptable acids but the salts of other acids of use in the purification or the isolation of the compounds of formula (I) also form part of the invention. The pharmaceutically acceptable salts of the compounds of formula (I) are, for example, the hydrochloride, the hydrobromide, the sulphate, the hydrogensulphate, the dihydrogenphosphate, the methanesulphonate, the benzenesulphonate, the naphthalenesulphonate, the para-toluenesulphonate, the maleate, the fumarate, the succinate, the citrate, the acetate, the gluconate or the oxalate.

A very particular subject-matter of the present invention is compounds of formula:

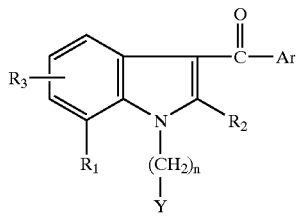
(I)

in which:
Ar represents:
  a) a phenyl mono-, di- or trisubstituted by one or more groups chosen from: a halogen atom, a $(C_1-C_4)$alkyl, a trifluoromethyl, an amino, a nitro, a $(C_1-C_4)$alkoxy, a $(C_1-C_4)$alkylsulphanyl or a $(C_1-C_4)$alkylsulphonyl;
  b) a naphthyl which is unsubstituted or substituted once or twice by a halogen atom, a $(C_1-C_4)$alkyl or a trifluoromethyl;
n represents 2, 3 or 4;
Y represents a group chosen from $SR_4$, $SOR_4$, $SO_2R_4$, $SO_2NR_5R_6$, $N(R_7)SO_2R_4$ or $OR_4$;
$R_1$ represents a halogen atom, a $(C_1-C_4)$alkyl, a trifluoromethyl or a $(C_1-C_4)$alkoxy;
$R_2$ represents hydrogen or a $(C_1-C_4)$alkyl;
$R_3$ represents hydrogen a $(C_1-C_4)$alkyl or a halogen;
$R_4$ represents a $(C_1-C_4)$alkyl;
$R_5$ and $R_6$ each independently represent hydrogen or a $(C_1-C_4)$alkyl;
$R_7$ represents hydrogen or a $(C_1-C_4)$alkyl;

and their optional salts and their solvates.

According to the present invention, preference is given to the compounds of formula (I) in which $R_1$ is in the 7 position of the indole nucleus and represents a methyl or chlorine or bromine atom and to the compounds of formula (I) in which $R_2$ represents a $(C_1-C_4)$alkyl, particularly a methyl.

The compounds of formula (I) in which $R_3$ is hydrogen or $R_3$ is in the 6 position of the indole nucleus and represents a chlorine atom or a methyl are preferred.

The compounds of formula (I) in which $R'_3$ is hydrogen are preferred.

The compounds of formula (I) in which Ar represents a phenyl mono- or disubstituted by a halogen atom, a methyl, a trifluoromethyl, a methoxy, a methylsulphanyl or a methylsulphonyl are preferred.

The compounds of formula (I) in which Y represents $SO_2R_4$ or $NHSO_2R_4$ are also preferred, particularly when $R_4$ represents a methyl or an ethyl.

Thus, preference is very particularly given to the compounds of formula (I) in which:
  Ar represents a phenyl mono- or disubstituted by a halogen atom, a methyl, a trifluoromethyl, a methoxy, a methylsulphanyl or a methylsulphonyl;
  A represents a $(CH_2)_n$ group;
  n represents 2, 3 or 4;
  Y represents $SO_2R_4$ or $NHSO_2R_4$;
  $R_1$ represents a methyl or a chlorine or bromine atom in the 7 position of the indole nucleus;
  $R_2$ represents a methyl;
  $R_3$ is hydrogen or $R_3$ represents either a chlorine atom or a methyl in the 6 position of the indole nucleus;
  $R'_3$ is hydrogen;
  $R_4$ represents a methyl or an ethyl;

and their optional salts and their solvates.

Another subject-matter of the present invention is the processes for the preparation of the compounds of formula (I), of their optional salts and of their solvates.

One process according to the invention, known as process A, is characterized in that:
a) an indole of formula:

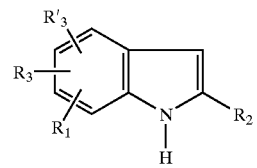
(II)

in which $R_1$, $R_2$, $R_3$ and $R'_3$ are as defined for a compound of formula (I), is treated with a methylmagnesium halide and with an acid halide of formula ArCOHal (III), in which Ar is as defined for the compound of formula (I) and Hal represents a halogen atom, preferably chlorine;
b) the compound thus obtained, of formula:

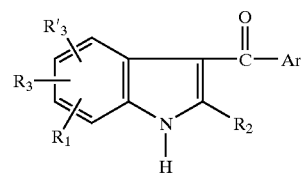
(IV)

is treated with a halide of formula Hal—A—Y (V), in which —A— and Y are as defined for a compound of formula (I) and Hal represents a halogen atom, preferably bromine, in the presence of a base.

If appropriate, the compound of formula (I) thus obtained is converted into one of its salts or solvates.

In stage a) of the above process, the acylation is carried out in an inert solvent, such as ether.

In stage b), the reaction is carried out in the presence of a base, such as sodium carbonate or potassium carbonate, a hydride, such as sodium hydride, or an alkali metal hydroxide, such as potassium hydroxide, and in a solvent, such as toluene, DMSO or DMF, at a temperature between ambient temperature and the boiling point of the solvent. Specifically, when the base used is an alkali metal hydroxide, stage b) can also be carried out in the presence of tris[2-(2-methoxyethoxy)ethyl]amine (TDA-1), as described in Tetrahedron Lett., 1987, 28, 2963 or of a quaternary ammonium salt, such as tetrabutylammonium hydrogensulphate.

There exists an alternative form of process A, known as process $A_1$, characterized in that stage b) of process A is modified in the following way:

b1) the compound obtained in stage a), of formula:

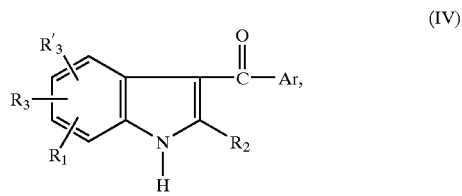

(IV)

is treated with a compound of formula Z—A—Cl (VI), in which Z represents either a hydroxyl group or a halogen atom, preferably bromine, and —A— is as defined for (I);

b2) optionally, the compound thus obtained, of formula:

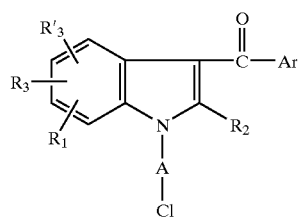

(VII)

is treated with sodium iodide;

b3) the compound thus obtained in stage b1, of formula (VII), or in stage b2), of formula:

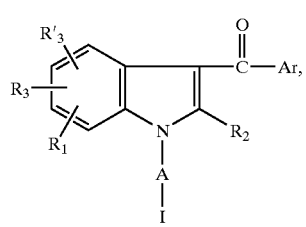

(VIII)

is treated with a Y anion, Y being as defined for a compound of formula (I), to form the compound of formula (I).

When Z represents a halogen atom, stage b1) is carried out in the presence of a base; when Z represents a hydroxyl group, stage b1) is carried out in the presence of triphenylphosphine and diethyl azodicarboxylate in a solvent such as dichloromethane.

In stage b2), when the latter is carried out, a solvent such as acetonitrile, acetone or another ketone is used.

Use is made, in carrying out stage b3), of an anion obtained by reaction of a compound of formula YH (IX) with NaH in a solvent such as DMF.

Process $A_1$ is particularly preferred for preparing compounds of formula (I) in which Y represents $SR_4$ or $NHSO_2R_4$.

According to another alternative form of process A, known as process $A_2$, it is possible to prepare a compound of formula (I) in which Y represents an $SOR_4$ group or an $SO_2R_4$ group, from a compound of formula (I) in which Y represents an $SR_4$ group. This process is characterized in that, after stage b) of process A or stage b2) or b3) of process $A_1$, the following additional stage is carried out:

c1) the compound obtained, of formula:

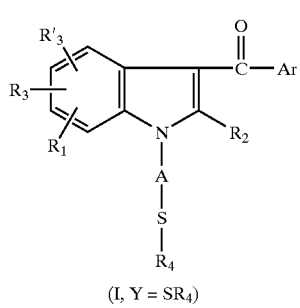

(I, Y = $SR_4$)

is treated with an oxidizing agent.

Use may be made, as oxidizing agent, of aqueous hydrogen peroxide solution or 3-chloroperbenzoic acid; depending upon the number of equivalents of oxidizing agent used and depending upon the reaction temperature, a sulphoxide (I, Y=$SOR_4$) or a sulphone (I, Y=$SO_2R_4$) is obtained.

According to another alternative form of process A, known as process $A_3$, it is possible to prepare a compound of formula (I) in which Y represents an $N(R_7)SO_2R_4$ group in which $R_7$ is other than H, from a compound of formula (I) in which Y represents an $NHSO_2R_4$ group. This process is characterized in that, after stage b) of process A or stage b2) or b3) of process $A_1$, the following additional stage is carried out:

c2) the compound obtained, of formula:

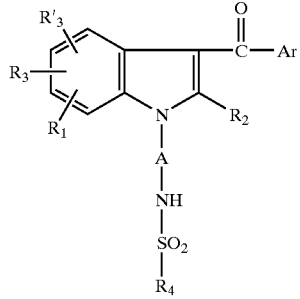

(I, Y = $NHSO_2R_4$)

is treated with an alkylating agent in the presence of a base.

Use is made, as alkylating agent, of, for example, a dialkyl sulphate of formula $SO_4(R_7)_2$ or an alkyl halide of formula $R_7Hal$, in which formulae $R_7$ is as defined for the compounds of formula (I) and Hal represents a halogen atom, preferably iodine, in the presence of a base, such as sodium hydride, for example.

According to yet another alternative form of process A, known as process $A_4$, it is possible to prepare a compound of formula (I) in which Y represents an $SO_2NR_5R_6$ group from a compound of formula (I) in which Y represents an $SO_2NHR_5$ group. This process is characterized in that, after stage b) of process A or stage b2) or b3) of process $A_1$, the following additional stage is carried out:

c3) the compound obtained, of formula:

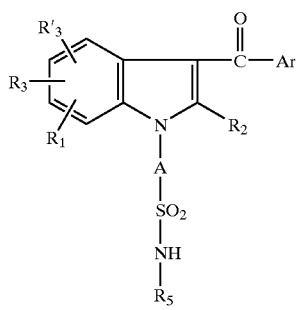

(I, Y = SO$_2$NHR$_5$)

is treated with an alkylating agent in the presence of a base.

Use is made, as alkylating agent, of, for example, a dialkyl sulphate of formula SO$_4$(R$_6$)$_2$ or an alkyl halide of formula R$_6$Hal, in which formulae R$_6$ is as defined for the compounds of formula (I) and Hal represents a halogen atom, preferably iodine, in the presence of a base, such as sodium hydride.

When it is desired to prepare a compound according to the invention of formula (I) in which Y represents an NR$_7$SO$_2$R$_4$ group or an NR$_7$SO$_2$NR$_5$R$_6$ group, use may be made of an alternative form of process A, known as process A5.

This process is characterized in that:

b4) the compound obtained in stage b1), of formula:

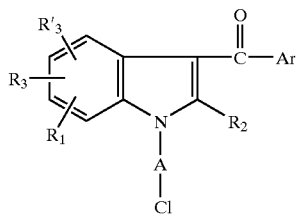

(VII)

is converted into a compound of formula:

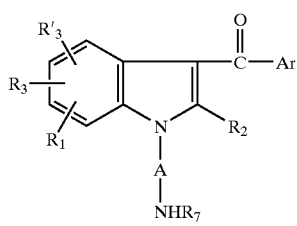

(XI)

in which R$_7$ is as defined for (I);

c4) treatment is carried out with a halide of formula HalSO$_2$R$_4$ or respectively HalSO$_2$NR$_5$R$_6$ in which R$_4$, R$_5$ and R$_6$ have the meanings given above for (I).

Stage b4) can be carried out by various processes known to a person skilled in the art, for example the Delépine reaction (Synthesis, 1979, p. 161–179), the Gabriel reaction (Angew. Chem. Int. Ed. Engl., 1998, 7, 919–930 or the Hebrard reaction (Bull. Soc. Chim. Fr., 1970, 1938).

Stage c4) can be carried out in the presence of a base, such as triethylamine.

According to an alternative method to process A described above and its alternative forms, it is possible to carry out first the alkylation of the indole nitrogen and then to carry out the acylation of the compound thus obtained. This alternative process, known as process B, is characterized in that:

i) an indole of formula:

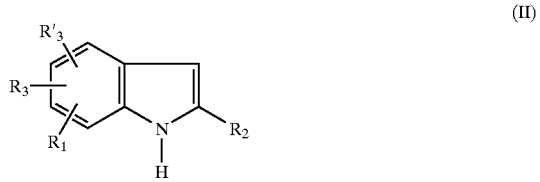

in which R$_1$, R$_2$, R$_3$ and R'$_3$ are as defined for the compound of formula (I), is treated with a halide of formula Hal—A—Y (V), in which —A— and Y are as defined for a compound of formula (I) and Hal represents a halogen atom, preferably bromine, in the presence of a base;

ii) the compound thus obtained, of formula:

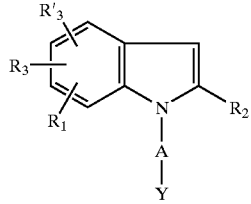

(XII)

is treated with an acid halide of formula ArCOHal (III) in which Ar is as defined for the compound of formula (I) and Hal is a halogen atom, preferably chlorine or bromine.

If appropriate, the compound of formula (I) thus obtained is converted into one of its salts or solvates.

Stage i) of the above process is carried out under the conditions described for stage b) of process A. Stage ii) is carried out under Friedel-Crafts conditions in the presence of a Lewis acid, such as AlCl$_3$ or ethylaluminium dichloride, in an inert solvent, such as dichloromethane or dichloroethane, according to the process described in J. Med. Chem., 1995, 38, 3094.

Various alternative forms of stage i) of process B exist. These alternative forms correspond to what was described for process A. These alternative forms also constitute a subject-matter of the present invention.

Thus, the alternative form B$_1$ of process B is characterized in that:

i1) an indole of formula:

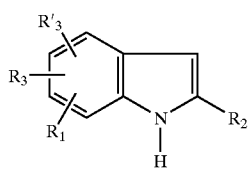

(II)

in which R$_1$, R$_2$ and R$_3$ are as defined for the compound of formula (I), is treated with a compound of formula Z—A—Cl (VI) in which —A— is as defined for the compound of formula (I) and Z represents a hydroxyl group or a halogen atom, preferably bromine;

i2) optionally, the compound thus obtained, of formula:

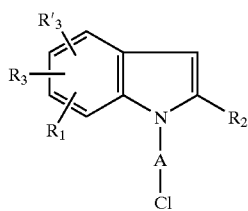

(XIII)

is treated with sodium iodide;

i3) the compound thus obtained in stage i1) or in stage i2), of formula:

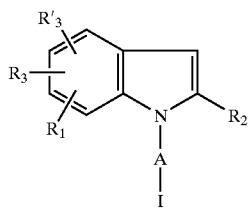

(XIV)

is treated with an anion of formula Y$^-$, Y being as defined for a compound of formula (I);

ii) the compound thus obtained, of formula:

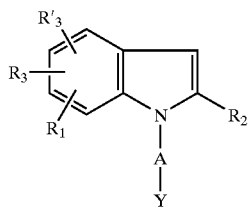

(XII)

is treated with an acid halide of formula ArCOHal (III) in which Ar is as defined for the compound of formula (I) and Hal is a halogen atom, preferably chlorine.

If appropriate, the compound of formula (I) thus obtained is converted into one of its salts or solvates.

Specifically, when it is desired to prepare a compound of formula (I) in which A is (CH$_2$)$_2$, use may be made of techniques known to a person skilled in the art for introducing the alkyl chain of appropriate length in one of the stages, either of method A or of method B.

The indoles of formula (II) are known or are prepared by known methods, such as described in J. Am. Chem. Soc., 1974, 96, 5495 and 1974, 96, 5512, or in Tetrahedron Lett., 1989, 30, 2129.

The indoles of formula:

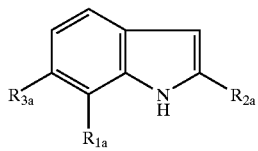

(IIa)

in which:

R$_{1a}$ represents a chlorine or bromine atom or a methyl;
R$_{2a}$ represents a (C$_1$–C$_4$)alkyl, preferably methyl;
R$_{3a}$ represents hydrogen, a chlorine or bromine atom, or a methyl;

are novel and constitute a subject-matter of the present invention.

The compounds of formula ARCOCl (III) are known or prepared by known methods.

The compounds of formula Hal(CH$_2$)$_n$Y (V) are known or prepared by known methods. For example, an ω-bromomethylsulphanylalkyl can be prepared from an ω-hydroxymethylsulphanylalkyl by the action of PBr$_3$.

The intermediate compounds of formula:

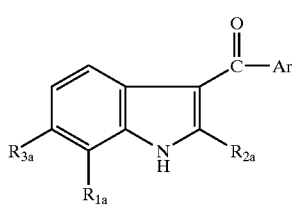

(IVa)

in which:

R$_{1a}$ represents a chlorine or bromine atom or a methyl;
R$_{2a}$ represents a (C$_1$–C$_4$)alkyl, preferably methyl;
R$_{3a}$ represents hydrogen, a chlorine or bromine atom, or a methyl;
Ar is as defined for the compounds of formula (I);

are novel and constitute a further subject-matter of the invention.

The intermediate compounds of formula:

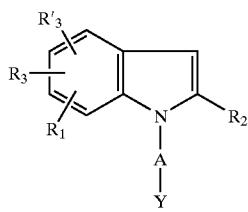

(XII)

in which $R_1$, $R_2$, $R_3$, Y and A are as defined for (I) are novel and represent a further subject-matter of the present invention.

The compounds according to the invention have shown a good in vitro affinity for ($CB_2$) cannabinoid receptors and a markedly weaker in vitro affinity for ($CB_1$) cannabinoid receptors, whether human receptors or rodent receptors. Affinity binding assays were carried out according to the experimental conditions described by Devane et al. (Molecular Pharmacology, 1988, 34, 605–613), with membranes resulting from cell line in which the $CB_1$ receptors (Matsuda et al., Nature, 1990, 346, 561–564) and the $CB_2$ receptors (Munro et al., Nature, 1993, 365, 61–65) were expressed. For human receptors, the in vitro affinity [lacuna] $CB_2$ cannabinoid [lacuna], expressed in the form of Ki (inhibition constant), is of the nM order and the ratio of the affinity for the $CB_1$ receptors to that for the $CB_2$ receptors is at least 100.

Furthermore, the compounds according to the invention behave in vitro as agonists specific for the human $CB_2$ cannabinoid receptors versus the human $CB_1$ cannabinoid receptors, they decrease the production of cAMP in cells stimulated by forskolin by inhibiting adenylate cyclase. The tests were carried out according to the experimental conditions described by Matsuda et al., Nature, 1990, 346, 561–564.

The compounds according to the invention also possess an in vivo affinity for the cannabinoid receptors present in the mouse spleen when they are administered orally. The tests were carried out according to the experimental conditions described by Rinaldi-Carmona et al., J. Pharmacol. Exp. Ther., 1998, 284, 644–650.

Thus, the compounds of Examples 7, 44, 46, 72, 89, 106, 120, 130 and 132, for which the ratio of the affinity for the $CB_1$ receptors to that for the $CB_2$ receptors is between 400 and 4 000, are active orally with an $ED_{50}$ of between 0.2 mg/kg and 20 mg/kg.

The compounds of the present invention are in particular active principles for pharmaceutical compositions, the toxicity of which is compatible with their use as medicaments.

According to one of its aspects, the present invention relates to the use of a compound of formula (I) or of one of its pharmaceutically acceptable salts or solvates in the preparation of medicaments intended to prevent or to treat any pathology in which $CB_2$ cannabinoid receptors are implicated.

Mention may be made, for example, of the following diseases or conditions:

disorders of the immune system, in particular autoimmune diseases: psoriasis, lupus erythematosus, diseases of the connective tissue, Sjögren's syndrome, ankylosing spondylarthritis, rhumatoid arthritis, reactional arthritis, undifferentiated spondylarthritis, Behcet's disease, autoimmune hemolytic anaemias, multiple sclerosis, amyotrophic lateral sclerosis, amyloses, graft rejection or diseases affecting the plasma cell line; allergic diseases: delayed or immediate hypersensitivity, allergic rhinitis, contact dermatitis or allergic conjunctivitis; infectious parasitic, viral or bacterial diseases: AIDS or meningitis; inflammatory diseases, in particular diseases of the joints: arthritis, rhumatoid arthritis, osteoarthritis, spondylitis, gout, vasculitis, Crohn's disease, inflammatory bowel disease (IBD) or irritable bowel syndrome (IBS); osteoporosis; pain: chronic pain of inflammatory type, neuropathic pain or acute peripheral pain; eye conditions: ocular hypertension or glaucoma; pulmonary conditions: diseases of the respiratory tract, asthma, chronic bronchitis, chronic obstructive pulmonary disease (COPD) or emphysema; diseases of the central nervous system and neurogenerative diseases: Tourette's syndrome, Parkinson's disease, Alzheimer's disease, senile dementia, chorea, Huntington's chorea, epilepsy, psychoses, depression or spinal cord lesions; migraine, vertigo, vomiting or nausea, in particular that resulting from a chemotherapy; cardiovascular diseases, in particular hypertension, arteriosclerosis, heart attack or cardiac ischaemia; renal ischaemia; cancers: benign skin tumours, cancerous tumours and papillomas, prostate tumours or brain tumours (glioblastomas, medulloepitheliomas, medulloblastomas, neuroblastomas, tumours of embryonic origin, astrocytomas, astroblastomas, ependymomas, oligodendrogliomas, plexus tumours, neuroepitheliomas, tumour of the epiphysis, ependymoblastomas, neuroectodermal [lacuna], malignant meningiomas, sarcomatoses, malignant melanomas or schwennomas); gastrointestinal diseases; or obesity.

The use of the compounds according to the invention for the prevention and/or treatment of the abovementioned diseases and in the preparation of medicaments intended to treat these diseases forms an integral part of the invention.

The compounds of formula (I) above, or one of their pharmaceutically acceptable salts or solvates, can be used at daily doses of 0.01 to 100 mg per kilo of body weight of the mammal to be treated, preferably at daily doses of 0.1 to 50 mg/kg. In man, the dose can preferably vary from 0.1 to 4 000 mg per day, more particularly from 0.5 to 1 000 mg, depending on the age of the subject to be treated or the type of treatment, prophylactic or curative.

For their use as medicaments, the compounds of formula (I) are generally administered in dosage units. The said dosage units are preferably formulated in pharmaceutical compositions in which the active principle is mixed with one or more pharmaceutical excipients.

Thus, according to another of its aspects, the present invention relates to pharmaceutical compositions including, as active principle, a compound of formula (I) or one of its pharmaceutically acceptable salts or solvates.

In the pharmaceutical compositions of the present invention for oral, sublingual, inhaled, subcutaneous, intramuscular, intravenous, transdermal, local or rectal administration, the active principles can be administered in unit administration forms, as a mixture with conventional pharmaceutical vehicles, to animals and to human beings. The appropriate unit administration forms comprise oral forms, such as tablets, gelatin capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

When a solid composition is prepared in the form of tablets or gelatin capsules, a mixture of pharmaceutical excipients is added to the micronized or non-micronized active principle, which mixture can be composed of diluents, such as, for example, lactose, mannitol, microcrystalline cellulose, starch or dicalcium phosphate, of binders, such as, for example, polyvinylpyrrolidone or hydroxypropylmethylcellulose, of disintegrating agents, such as crosslinked polyvinylpyrrolidone, crosslinked carboxymethylcellulose or sodium croscarmellose, of flow agents, such as silica or talc, or of lubricants, such as magnesium stearate, stearic acid, glyceryl tribehenate or sodium stearylfumarate.

Wetting agents or surface-active agents, such as sodium lauryl sulphate, polysorbate 80 or poloxamer 188, can be added to the formulation.

The tablets can be prepared by various techniques: direct tableting, dry granulation, wet granulation or hot melt.

The tablets can be plain or sugar-coated (with sucrose, for example) or coated with various polymers or other appropriate materials.

The tablets can have immediate, delayed or sustained release by preparing polymer matrices or by using specific polymers in the film coating.

The gelatin capsules can be soft or hard and may or may not be film-coated, so as to have an immediate, sustained or delayed activity (for example via an enteric form).

They can comprise not only a solid formulation formulated as above for tablets but also liquids or semisolids.

A preparation in the syrup or elixir form can comprise the active principle in conjunction with a sweetener, preferably a calorie-free sweetener, methylparaben and propylparaben as antiseptic, a flavour enhancer and an appropriate colorant.

The water-dispersible powders or granules can comprise the active principle as a mixture with dispersing agents, wetting agents or suspending agents, such as polyvinylpyrrolidone, and with sweeteners or flavour enhancers.

For rectal administration, recourse is had to suppositories which are prepared with binders which melt at the rectal temperature, for example cocoa butter or polyethylene glycols.

For parenteral, intranasal or intraocular administration, use is made of aqueous suspensions, isotonic saline solutions or sterile injectable solutions which comprise pharmacologically compatible dispersing agents and/or solubilizing agents, for example propylene glycol.

Thus, to prepare an aqueous solution for intravenous injection, it is possible to use a cosolvent, such as, for example, an alcohol, such as ethanol, or a glycol, such as polyethylene glycol or propylene glycol, and a hydrophilic surfactant, such as polysorbate 80 or poloxamer 188. To prepare an oily solution for intramuscular injection, the active principle can be dissolved with a triglyceride or a glycerol ester.

For local administration, creams, ointments, gels, eyewashes or sprays can be used.

For transdermal administration, use may be made of patches in the multilayer form or in the reservoir form, in which the active principle can be in alcoholic solution, or sprays.

For administration by inhalation, use is made of an aerosol comprising, for example, sorbitan trioleate or oleic acid, and trichlorofluoromethane, dichlorofluoromethane, dichlorotetrafluoroethane, freon substitutes or any other biologically compatible propellant gas; use may also be made of a system comprising the active principle alone or in combination with an excipient, in the powder form.

The active principle can also be presented in the form of a complex with a cyclodextrin, for example α-, β- or γ-cyclodextrin or 2-hydroxypropyl-β-cyclodextrin.

The active principle can also be formulated in the form of microcapsules or microspheres, optionally with one or more vehicles or additives.

Use may be made, among the sustained-release forms of use in the case of chronic treatments, of implants. These can be prepared in the form of an oily suspension or in the form of a suspension of microspheres in an isotonic medium.

In each dosage unit, the active principle of formula (I) is present in the amounts appropriate for the daily doses envisaged. Generally, each dosage unit is suitably adjusted according to the dosage and the type of administration anticipated, for example tablets, gelatin capsules and the like, sachets, vials, syrups and the like, or drops, so that such a dosage unit comprises from 0.1 to 1 000 mg of active principle, preferably from 0.5 to 250 mg, which have to be administered one to four times daily.

Although these dosages are examples of average situations, there may be specific cases where higher or lower dosages are appropriate; such doses also come within the invention. According to the usual practice, the dosage appropriate for each patient is determined by the doctor according to the method of administration and the age, weight and response of the said patient.

The compositions of the present invention can comprise, in addition to the compounds of formula (I) or one of their pharmaceutically acceptable salts, solvates and/or hydrates, other active principles which may be of use in the treatment of the disorders or diseases indicated above.

Thus, another subject-matter of the present invention is pharmaceutical compositions comprising several active principles in combination, one of which is a compound according to the invention.

The compounds according to the invention can also be used in the preparation of compositions for veterinary use.

Furthermore, the compounds according to the invention, as such or in the radiolabelled form, can be used as pharmacological tools in man or in animals or in the detection and the labelling of $CB_2$ cannabinoid receptors.

The following PREPARATIONS and EXAMPLES illustrate the invention without, however, limiting it.

In the Preparations and the Examples, the following abbreviations are used:

ether: diethyl ether
iso ether: diisopropyl ether
DMF: N,N-dimethylformamide
THF: tetrahydrofuran
DCM: dichloromethane
AcOEt: ethyl acetate
TDA-1: tris[2-(2-methoxyethoxy)ethyl]amine
Hydrochloric ether: saturated solution of hydrochloric acid in diethyl ether
Triton B: N-benzyltrimethylammonium hydroxide
M.p.: melting point
AT: ambient temperature
B.p.: boiling point The proton magnetic resonance spectra ($^1$H NMR) are recorded at 200 MHz in $d_6$-DMSO using the $d_6$-DMSO peak as reference. The chemical shifts δ are expressed in parts per million (ppm). The signals observed are expressed thus: s: singlet; bs: broad singlet; d: doublet; d.d: double doublet; t: triplet; dt: double triplet; q: quartet; qt: quintet; m: unresolved peak; mt: multiplet; sp: septet.

Preparation of the indoles of formula (II).

Preparation 1.1

2-Methyl-7-chloro-1H-indole.

42.1 g of 2-chloronitrobenzene are placed in 850 ml of THF under a nitrogen atmosphere. The mixture is cooled to −40° C. and then 1.61 of 0.5M isopropenylmagnesium bromide in THF are added dropwise. After stirring at −40° C. for 1 hour, the mixture is hydrolysed with 400 ml of a saturated $NH_4Cl$ solution. The aqueous phase is extracted twice with ether. The organic phase is dried and then evaporated and the residue is chromatographed on silica while eluting with toluene. 20.3 g of the expected compound are obtained.

NMR:δ (ppm):2.4:s:3H; 6.2:s:1H; 6.9:t:1H; 7.1:d:1H; 7.4:d:1H; 11.2:bs:1H.

Preparation 1.2

2-Methyl-7-isopropyl-1H-indole.

1 570 ml of a 0.5M solution of isopropenylmagnesium bromide in THF are prepared and are cooled to −45° C. This cooled solution is run slowly onto a solution of 43.3 g of 2-isopropylnitrobenzene in 400 ml of THF placed under nitrogen. The reaction medium is cooled to −40° C. and then stirring is maintained at this temperature for 1 hour and a half. The reaction medium is poured onto 1 liter of saturated $NH_4Cl$ solution. The aqueous phase is extract twice with ether and then with DCM; washing is carried out with a saturated NaCl solution. The organic phase is dried and then evaporated and the residue is chromatographed on silica while eluting with an AcOEt/cyclohexane (2/8, v/v) mixture. 23.7 g of the expected compound are obtained.

NMR:δ (ppm):1.1:d:6H; 2.4:s:3H; 3.3:mt:1H; 6:s:1H; 6.7 and 7.2:2 mt:3H; 10.8:bs:1H.

Preparation 1.3

7-Bromo-2-ethyl-1H-indole.

2.4 g of magnesium are placed in a round-bottomed flask and the magnesium is covered with 10 ml of THF. 1 g of 2-bromo-1-butene, then 10 ml of THF and then again 12.5 g of 2-bromo-1-butene in 30 ml of THF are added. The reaction medium is observed to warm up and then it is heated at 60° C. for 30 minutes after the end of the addition reaction. The mixture is subsequently cooled to −20° C., 20 ml of THF are added and then 6.7 g of 2-bromonitrobenzene are added at −20° C. The mixture is allowed to return to AT. The reaction medium is poured onto 200 ml of a saturated NaCl solution. Extraction is carried out with ether, the extracts are then evaporated and the residue is taken up in DCM. The organic phase is washed with water and then with a saturated NaCl solution. It is dried and evaporated and then the residue is chromatographed on silica while eluting with a cyclohexane/AcOEt (9.5/0.5, v/v) mixture. 3.45 g of the expected compound are obtained.

NMR:δ (ppm):1.3:t:3H; 2.8:q:2H; 6.2:s:1H; 6.8:t:1H; 7.2:d:1H7.4:d:1H; 11:bs:1H.

Preparation 1.4

2-Methyl-7-ethyl- 1H-indole.

A solution of 36.5 g of 2-ethylnitrobenzene in 250 ml of THF is added dropwise at −20° C. to 1.6 l of 0.5M isopropenylmagnesium bromide in THF. The reaction medium is maintained at −20° C. with stirring for 2 hours and then the medium is poured onto 800 ml of saturated NaCl solution. The mixture is allowed to separate by settling and then extraction is carried out with ether. The ether extract is dried and evaporated and then the residue is chromatographed on silica while eluting with an AcOEt/cyclohexane (1/9, v/v) mixture. 23.75 g of the expected compound are obtained.

NMR:δ (ppm):1.3:t:3H; 2.4:s:3H; 2.8:q:2H; 6.2:s:1H; 6.8:m:2H; 7.2:d:1H; 10.8:bs:1H.

Preparation 1.5

7-Bromo-2-methyl-1H-indole.

27.0 g of 2-bromonitrobenzene are placed in 400 ml of THF. The medium is placed under nitrogen and is cooled to −55° C. and then 800 ml of 0.5M isopropenylmagnesium bromide in THF are added dropwise. The medium is left stirring for 1 hour and then it is poured into a saturated $NH_4Cl$ solution. Extraction is carried out with ether, the extract is evaporated and then the residue is taken up in DCM. Washing is carried out with a saturated NaCl solution. The organic layer is dried and evaporated and then the residue is chromatographed on silica while eluting with an AcOEt/cyclohexane (1/9, v/v) mixture. 10.7 g of the expected compound are obtained.

NMR:δ (ppm):2.4:s:3H; 6.2:s:1H; 6.9:t:1H; 7.2:d:1H; 7.4:d:1H11.2:bs:1H.

Preparation 1.6

6,7-Dichloro-2-methyl-1H-indole.

1 600 ml of 0.5M isopropenylmagnesium bromide in THF are introduced under nitrogen and are cooled to −20° C., 51.2 g of 2,3-dichloronitrobenzene in 250 ml of anhydrous THF are added and the mixture is left stirring for I hour at −20° C. The reaction medium is poured at −20° C. onto 1 liter of saturated $NH_4Cl$ solution, the mixture is diluted with $Et_2O$ and then the aqueous phase is washed twice with $Et_2O$. The organic phases are combined and are concentrated to dryness. The residue is extracted with DCM and the organic phase is washed twice with water and then with a saturated NaCl solution. It is dried and then evaporated and the residue is chromatographed on [lacuna] a hexane/AcOEt (95/5, v/v) mixture. 24.27 g of the expected compound are obtained, M.p.=70–71° C.

The indole derivatives described in Table 1 below were also prepared:

TABLE 1

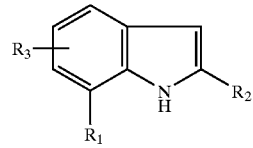

| Preparations | $R_1$ | $R_2$ | $R_3$ | M.p.(° C.)/NMR:δ (ppm) |
|---|---|---|---|---|
| 1.7 | Cl | Me | 5-Cl | 56° C. |
| 1.8 | Br | Me | 6-Me | 67–68° C. |
| 1.9 | Cl | Me | 6-Me | 2.35:s:3H; 3.85:s:3H; 6.15:s:1H; 6.85:d:1H; 7.15:d:1H; 11.20:s:1H |
| 1.10 | Me | Me | 6-Cl | 2.40:s:3H; 2.45:s:3H; 6.15:s:1H; 7:d:1H; 7.30:d:4H; 11:s:1H |
| 1.11 | F | Me | H | 2.40:s:3H; 6.20:mt:1H; 6.70–7.30:m:3H; 11.30:s:1H |
| 1.12 | Br | Et | H | 1.20:t:3H; 2.70:g:2H; |
| 1.13 | Et | Me | H | 1.2:t:3H; 2.30:s:3H; 2.75:q:2H; 6.00:s:1H; 6.60–7.20:m:3H; 10.70:bs:1H |
| 1.14 | Cl | Et | H | 1.30:t:3H; 2.80:q:2H; 6.25:s:1H; 6.80–7.60:m:3H; 11.20:bs:1H |
| 1.15 | Cl | Me | 4-Cl | 2.40:s:3H; 6.20:s:1H; 6.80–7.10:m:2H; 11.55:bs:1H |
| 1.16 | Cl | Me | 4-Me | 2.35:s:6H; 6.15:s:1H; 6.65:d:1H; 6.85:d:1H; 11.05:bs:1H |

EXAMPLE 1

(Process B)

(7-Chloro-2-methyl-1-(3-(methylsulphanyl)propyl)-1H-indol-3-yl)(2,3-dichloro-phenyl)methanone I: $R_1$=Cl, $R_2$=Me, $R_3$=R'$_3$=H, Ar=2,3-dichlorophenyl, Y=—S—Me, A=$(CH_2)_n$, n=3.

A) 1-Bromo-3-methylsulphanylpropane.

24 g of $PBr_3$ are mixed at 0° C., with stirring, with 20 g of 3-(methylsulphanyl)-1-propanol. The medium is allowed to return to AT and then it is heated at 100° C. for 1 hour. It is allowed to cool to AT and then it is cooled in an ice bath. The medium is taken up in benzene and then is extracted with toluene. The extract is washed with a 1% $Na_2CO_3$ solution, with water and then with a saturated NaCl solution. It is dried over $MgSO_4$ and concentrated, and then distillation is carried out to produce 3.6 g of the expected compound.

B) 7-Chloro-2-methyl-1-(3-(methylsulphanyl)propyl)-1H-indole.

1.5 g of 7-chloro-2-methyl-1H-indole are mixed with stirring with 1.1 g of ground potassium hydroxide and 0.2 g of TDA-1. The mixture is left stirring for 2 hours at AT, then 3.1 g of 1-bromo-3-methylsulphanylpropane are added dropwise and the mixture is heated at reflux for 24 hours. Ground potassium hydroxide (0.5 g), TDA-1 (0.1 g) and 1.6 g of 1-bromo-3-methylsulphanylpropane are again added. After heating at reflux for 9 hours, 1.6 g of 1-bromo-3-methylsulphanylpropane are again added and the mixture is heated at reflux for 24 hours. The mixture is allowed to return to AT and is then extracted with toluene. The organic phase is washed with a 10% HCl solution, with water and then a saturated NaCl solution. It is dried and evaporated and then the residue is chromatographed on silica while eluting with a cyclohexane/toluene (50/50, v/v) mixture. 1.87 g of the expected compound are obtained.

NMR:δ (ppm):1.9:mt:2H; 2.1:s:3H; 2.4:s:3H; 2.5:mt:2H; 4.5:t:2H; 6.3:s:1H; 6.9:t:1H; 7.1:d:1H; 7.4:d:1H.

C) (7-Chloro-2-methyl-1-(3-(methylsulphanyl)propyl)-1H-indol-3-yl)-(2,3-dichloro-phenyl)methanone.

1.87 g of the compound in the preceding stage, in 50 ml of DCM, and 2.06 g of 2,3-dichlorobenzoyl chloride are mixed, while stirring, under a nitrogen atmosphere. The temperature is lowered to −5° C. and then 9 ml of 1.8M dichloroethylaluminium in toluene are added dropwise. The mixture is allowed to return to AT and is kept stirred for 24 hours. The medium is extracted with DCM and the organic phase is washed with a saturated $NH_4Cl$ solution, with water and then a saturated NaCl solution. It is dried and evaporated and then the residue is chromatographed on silica while eluting with a cyclohexane/toluene (50/50, v/v) mixture. The product obtained is crystallized from an ethanol/heptane mixture. 900 mg of the expected compound are obtained, M.p.=87° C.

NMR:δ (ppm):2:qt:2H; 2.1:s:3H; 2.4:s:3H; 2.6:t:2H; 4.6:mt:2H; 7 to 7.9:m:6H.

EXAMPLE 2

(Process $A_2$)

(7-Chloro-2-methyl-1-(3-(methylsulphonyl)propyl)-1H-indol-3-yl)2,3-dichloro-phenyl)methanone.

I: $R_1$=Cl, $R_2$=Me, $R_3$=R'$_3$=H, Ar=2,3-dichlorophenyl, Y=$SO_2$Me, A=$(CH_2)_n$, n=3.

0.73 g of the compound of Example 1 is placed in 5 ml of DCM. The temperature is lowered to 0° C., 1.03 g of 3-chloroperbenzoic acid, diluted in 10 ml of DCM, are then added dropwise and the mixture is left stirring for 24 hours at AT. The medium is extracted with DCM and then the extract is washed with a 5% $Na_2CO_3$ solution, with water and then with a saturated NaCl solution. It is dried and evaporated; the product obtained is crystallized from an ether/hexane mixture. 530 mg of the expected compound are obtained, M.p.=127° C.

NMR:δ (ppm):2.2:mt:2H; 2.4:s:3H; 3.0:s:3H; 3.3:mt:3H; 4.7:t:2H; 7.1:t:1H; 7.2 to 7.6:m:4H; 7.8:dd:1H.

EXAMPLE 3

(Process $B_1$)

N-(3-(7-Chloro-3-(2-fluoro-3-trifluoromethylphenyl)-2-methyl-1H-indol-1-yl)propyl)methanesulphonamide I: $R_1$=Cl, $R_2$=Me, $R_3$=R'$_3$=H, Ar=2-fluoro-3-trifluoromethylphenyl, Y=$NHSO_2$Me, A=$(CH_2)_n$, n=3.

A) 7-Chloro-1-chloropropyl-2-methyl-1H-indole.

40 g of 7-chloro-2-methyl-1H-indole are placed in 60 ml of toluene with 2.8 g of KOH under nitrogen. After stirring for 30 minutes at AT, 7.7 g of 3-chloro-1-bromopropane are added and then the mixture is heated to reflux for 3 hours. The medium is extracted with ether. The organic phase is washed with water, with a 10% HCl solution, with water and with a saturated NaCl solution. It is dried and evaporated and 6.19 g of the expected compound are obtained.

B) N-(3-(7-Chloro-2-methyl-1H-indol-1-yl)propyl)methanesulphonamide

A mixture comprising 2.2 g of 60% NaH in oil and 170 ml of DMF is prepared under nitrogen and is cooled to 0° C. 4.0 g of $NH_2SO_2CH_3$ are added, then the mixture is allowed to return to AT and 5.0 g of the compound of the preceding stage are added. The mixture is heated at 130° C. for 6 hours. The medium is extracted with DCM and the organic phase is washed with water and then with a saturated NaCl solution. It is dried and evaporated and then the residue is chromatographed on silica while eluting with a cyclohexane/AcOEt (30/70, v/v) mixture. 1.92 g of the expected compound are obtained.

C) N-(3-(7-Chloro-3-(2-fluoro-3-trifluoromethylphenyl)-2-methyl-1H-indol-1-yl)propyl)methanesulphonamide.

The mixing is carried out, under nitrogen, of 0.80 g of the compound of the preceding stage and 0.90 g of 2-fluoro-3-trifluoromethylbenzoyl chloride in 60 ml of DCM. The temperature is lowered to 0° C. and then 34 ml of 1.8M dichloroethylaluminium in toluene are added. The medium is allowed to return to AT and is then stirred for 15 hours. It is extracted with DCM. The organic phase is washed with water and with a saturated NaCl solution. It is dried and evaporated. The product is crystallized from a DCM/ether mixture. 550 mg of the expected compound are obtained, M.p.=168° C.

NMR:δ (ppm):2:mt:2H; 2.4:s:3H; 3.0:s:3H; 3.2:mt:2H; 4.7:mt:2H; 7 to 7.5:m:3H; 7.7:t:1H; 8:t:1H; 8.2:t:1H.

EXAMPLE 4

(Process A)

(7-Isopropyl-2-methyl-1-((2-ethylsulphanyl)ethyl)-1H-indol-3-yl)(2,3-dichlorophenyl)methanone I: $R_1$=iPr, $R_2$=Me, $R_3$=$R'_3$=H, Ar=2,3-dichlorophenyl, Y=—S-Et, A=$(CH_2)_n$, n=2

A) (7-Isopropyl-2-methyl-1H-indol-3-yl)-(2,3-dichlorophenyl)methanone.

120 ml of anhydrous THF are cooled to −5° C. and 36 ml of 3M methylmagnesium bromide in ether are added. The mixture is cooled to −30° C. and then 15 g of 7-isopropyl-2-methyl-1H-indole are added dropwise. The mixture is left stirring for 1 hour between −20° C. and −30° C. and then 30.9 g of 2,3-dichlorobenzoyl chloride, dissolved in 120 ml of THF, are added dropwise. The medium is left to return to AT and is then poured onto 300 ml of a saturated $NH_4Cl$ solution. Separation is carried out by settling, the organic layer is evaporated and then the residue is taken up in DCM. The organic phase is washed with a saturated NaCl solution and then it is dried and evaporated. The residue is chromatographed on silica while eluting with an AcOEt/cyclohexane (3/7, v/v) mixture.

B) (7-Isopropyl-2-methyl-1-((2-ethylsulphanyl)ethyl)-1H-indol-3-yl)(2,3-dichlorophenyl)methanone.

0.7 g of crushed sodium hydroxide, 1.5 g of the compound of the preceding stage, 0.15 g of tetrabutylammonium hydrogensulphate and 2.2 g of 1-chloro-1-ethylsulphanylethane are mixed. 60 ml of toluene and 0.2 g of water are added and the mixture is heated at reflux for 3 days. The medium is cooled and then it is poured onto water (200 ml). Extraction is carried out with 100 ml of ether and the organic phase is washed with water and then with a saturated NaCl solution. The organic phase is dried and evaporated and then the residue is chromatographed on silica while eluting with an AcOEt/cyclohexane (15/85, v/v) mixture. 0.85 g of the expected compound is obtained.

NMR:δ (ppm):1.1:t:3H; 1.25:d:6H; 2.3 to 2.6: m:5H; 2.8:t:2H3.45:sp:1H; 4.4:t:2H; 6.9 to 7.8:m:6H.

EXAMPLE 5

(Process A)

(7-Bromo-2-methyl-1-(3-(methylsulphanyl)propyl)-1H-indol-3-yl)(2,3-dichlorophenylmethanone)

I: $R_1$=Br, $R_2$=Me, $R_3$=$R'_3$=H, Ar=2,3-dichlorophenyl, Y=S—$CH_3$, A=$(CH_2)_n$, n=3.

A) (7-Bromo-2-methyl-1H-indol-3-yl)(2,3-dichlorophenyl-methanone).

10.7 g of 7-bromo-2-methyl-1H-indole are placed in 100 ml of THF and the mixture is cooled to −10° C. 22 ml of 3M methylmagnesium bromide in ether are added at this temperature. The mixture is allowed to return to AT and is then cooled to −5° C. and 13.5 g of 2,3-dichlorobenzoyl chloride, dissolved in 80 ml of THF, are added dropwise. The medium is allowed to return to AT and is then poured onto a saturated $NH_4Cl$ solution. Extraction is carried out with ether and then the organic phase is washed with a 10% NaOH solution, water and a saturated NaCl solution. It is dried and evaporated and the residue is chromatographed on silica while eluting with an AcOEt/cyclohexane (10/90, v/v) mixture. The product obtained crystallizes from ether and 5 g of the expected compound are obtained.

B) (7-Bromo-2-methyl-1-(3-chloropropyl)-1H-indol-3-yl) (2,3-dichlorophenyl)-methanone.

3 g of the compound of the preceding stage, 0.3 g of TDA-1 and 100 ml of toluene are added to 1 g of crushed potassium hydroxide, the mixture is then heated at reflux for 30 minutes and 5 g of 1-bromo-3-chloropropane are added. The medium is allowed to cool to AT and then it is poured onto 100 ml of a 10% HCl solution. The medium is extracted with toluene and then the organic phase is washed with water and then with a saturated NaCl solution. It is dried and evaporated and then the residue is chromatographed on silica while eluting with DCM. 3.25 g of the expected compound are obtained, M.p.=139° C.

C) (7-Bromo-2-methyl-1-(3-(methylsulphanyl)propyl)-1H-indol-3-yl)(2,3-dichlorophenylmethanone).

3 g of the compound of the preceding stage and 0.62 g of MeSNa are mixed at AT in 40 ml of ethanol. The mixture is heated at reflux for 2 and a half hours and then it is allowed to cool. The medium is poured onto a 10% sodium hydroxide solution. The medium is extracted with ether and then the organic phase is washed with a saturated NaCl solution. 2 g of the expected compound are obtained, M.p.=119° C.

NMR:δ (ppm):2:mt:2H; 2.1:s:3H; 2.4:s:3H; 2.6:t:2H; 4.6: t:2H; 7:t:1H; 7.4 to 7.6:m:4H; 7.8:dd:1H.

EXAMPLE 6

(Process $A_2$)

7-Bromo-2-methyl-1-(3-(methylsulphinyl)propyl)-1H-indol-3-yl)(2,3-dichlorophenyl)methanone I: $R_1$=Br, $R_2$=Me, $R_3$=$R'_3$=H, Ar=2,3-dichlorophenyl, Y=—SOMe, A=$(CH_2)_n$, n=3.

2.5 g of the compound of the preceding example are placed in 50 ml of acetic acid and the mixture is cooled to 10° C. 0.8 ml of $H_2O_2$ is added with stirring, then the mixture is allowed to return to AT and stirring is maintained for 1 and a half hours. The medium is evaporated and then extracted with AcOEt. The organic phase is washed with a 10% NaOH solution, water and a saturated NaCl solution. It is evaporated and the product obtained is recrystallized from an AcOEt/MeOH (9/1, v/v) mixture. 1.1 g of the expected compound are obtained, M.p.=137° C.

NMR:δ (ppm):2.1:qt:2H; 2.4 and 2.6:2s:6H; 2.8 to 3.2: mt:2H; 4.8:t:2H; 7.1:t:1H; 7.5:m:4H; 7.9:d:1H.

EXAMPLE 7

(Process $A_2$)

(7-Bromo-2-methyl-1-(3-(methylsulphonyl)propyl)-1H-indol-3-yl)(2,3-dichlorophenyl)methanone I: $R_1$=Cl, $R_2$=Me, $R_3$=$R'_3$=H, Ar=2,3-dichlorophenyl, Y=$SO_2$Me, A=$(CH_2)_n$, n=3.

1.82 g of 3-chloroperbenzoic acid are placed in 40 ml of DCM, the mixture is cooled to 0° C. and then 1.5 g of the compound of Example 5, dissolved in 30 ml of DCM, are added dropwise at 0° C. The mixture is allowed to return to AT and then stirring is maintained for 2 hours. After standing for 48 hours, the precipitate formed (excess acid) is filtered off and then the filtrate is poured into a 30% NaOH solution. The medium is extracted twice with $Et_2O$. The organic phase is washed with water and then with a saturated NaCl solution. It is dried and evaporated and then the residue is chromatographed on silica while eluting with AcOEt. 0.92 g of the expected compound is obtained, M.p.=90° C.

NMR:δ (ppm):2.2:mt:2H; 2.4:s:3H; 3:s:3H; 3.3:t:2H; 4.7: t:2H; 6.9 to 8:m:6H.

EXAMPLE 8

(Process $A_1$)

N-(3-(7-Bromo-3-(2,3-dichlorobenzoyl)-2-ethyl-1H-indol-1-yl)propyl)methane-sulphonamide I: $R_1$=Br, $R_2$=Et, $R_3$=$R'_3$=H, Ar=2,3-dichlorophenyl, Y=$NHSO_2Me$, A=$(CH_2)_n$, n=3

A) (7-Bromo-2-ethyl-1H-indol-3-yl)-(2,3-dichlorophenyl) methanone.

3.45 g of 7-bromo-2-ethyl-1H-indole are placed under nitrogen in 30 ml of ether and the mixture is cooled to +3° C.; 5.1 ml of methylmagnesium iodide in 20 ml of ether and then 5.9 g of dichlorobenzoyl chloride in 30 ml of ether are added. 10 ml of THF are added and the mixture is allowed to return to AT and is stirred for 3 hours. The medium is poured onto a saturated $NH_4Cl$ solution and is then extracted with ether. The organic phase is washed with a 10% HCl solution, a 10% NaOH solution, water and an NaCl solution. It is dried and evaporated and then the residue is chromatographed on silica while eluting with an AcOEt/cyclohexane (3/7, v/v) mixture. 2.18 g of the expected compound are obtained.

NMR:δ (ppm):1:t:3H; 2.8:q:2H; 6.9:t:1H; 7.1:d:1H; 7.2 to 7.6:m:3H; 7.8:dd:1H; 12.2:bs:1H.

B) (7-Bromo-1-(3-chloropropyl)-2-ethyl-1H-indol-3-yl)(2,3-dichlorophenyl)-methanone.

1.85 g of the compound of the preceding stage are placed in 100 ml of toluene with 0.3 g of TDA-1, 1 g of crushed potassium hydroxide is introduced, then the mixture is heated to reflux under nitrogen and 3.2 g of 3-bromo-1-chloropropane, diluted in 15 ml of toluene, are added. The mixture is heated overnight at reflux and then the reaction mixture is run quickly onto water. Extraction is carried out with toluene and the extract is washed with water and then with a saturated NaCl solution. The extract is dried and evaporated and then the residue is chromatographed on silica while eluting with an AcOEt/cyclohexane (3/7, v/v) mixture. 2 g of the expected compound are obtained.

C) (7-Bromo-1-(3-iodopropyl)-2-ethyl-1H-indol-3-yl)(2,3-dichlorophenyl)-methanone.

2.0 g of the compound of the preceding stage and 4.4 g of NaI are mixed in 120 ml of $CH_3CN$ and then the reaction is heated at 80° C. for 5 days. An NaCl precipitate is formed. The reaction medium is poured onto water, then extraction is carried out with toluene and the extract is washed with a saturated NaCl solution. 2.4 g of the expected compound are obtained.

D) N-(3-(7-Bromo-3-(2,3-dichlorobenzoyl)-2-ethyl-1H-indol-1-yl)propyl)methane-sulphonamide.

0.74 g of 60% NaH in oil is added to 80 ml of DMF and the mixture is cooled to +5° C. 2 g of $MeSO_2NH_2$ in 50 ml of DMF are added and the mixture is stirred for 10 minutes. 2.4 g of the compound of the preceding stage, in 40 ml of DMF, are then added and the mixture is left stirring for 3 hours at +5° C. The reaction medium is run quickly onto water and then extracted with DCM. The extract is washed with water and then with a concentrated NaCl solution. It is dried and evaporated and then the residue is chromatographed on silica while eluting with AcOEt/cyclohexane (1/1). 1.1 g of the expected compound are obtained.

NMR:δ (ppm):1.05:t:3H; 1.9:mt:2H; 2.65 to 3.2:m:7H; 4.5:mt:2H; 6.7 to 7.8:m:6H.

EXAMPLE 9

(Process $A_3$)

N-(3-(7-Bromo-3-(2,3-dichlorobenzoyl)-2-ethyl-1H-indol-1-yl)propyl)-N-methylmethanesulphonamide I: $R_1$=Br, $R_2$=Et, $R_3$=$R'_3$=H, Ar=2,3-dichlorophenyl, Y=$NMeSO_2Me$, A=$(CH_2)_n$, n=3.

0.32 g of NaH is placed in 20 ml of anhydrous DMF, and 0.86 g of the compound of the preceding example, dissolved in 20 ml of DMF, is added dropwise. Evolution of gas is observed. 1.15 g of MeI in 20 ml of DMF are added dropwise and the reaction medium is left stirring for 2 hours. The reaction medium is poured onto water and then separation by settling is carried out. Extraction is carried out with DCM and then the organic phase is washed with a saturated NaCl solution. It is dried and evaporated and the residue is chromatographed on silica while eluting with an AcOEt/cyclohexane (2/1, v/v) mixture. 0.5 g of the expected compound is obtained, M.p.=111° C.

NMR:δ (ppm):1.1:t:3H; 1.95:mt:2H; 2.6 to 3:m:8H; 3.2: t:2H; 4.5:mt:2H; 6.8 to 7.9: m:6H.

EXAMPLE 10

(Process A)

3-(3-(2,3-Dichlorobenzoyl)-7-ethyl-2-methyl-1H-indol-1-yl)-N,N-dimethyl-1-propane sulphonamide I: $R_1$=Et, $R_2$=Me, $R_3$=$R'_3$=H, Ar=2,3-dichlorophenyl, Y=—$SO_2NMe_2$, A=$(CH_2)_n$, n=3.

A) 3-Chloro-N,N-dimethyl-1-propanesulphonamide.

The product is prepared according to J. Am. Chem. Soc., 1951, 73, 3100.

10 g of dimethylamine hydrochloride are placed in 60 ml of water, a nitrogen atmosphere is applied and the solution is cooled to between 0° C. and −5° C., and then 18 ml of 3-chloro-1-propanesulphonyl chloride are added dropwise. 10.6 g of sodium hydroxide in 40 ml of water are added while maintaining at −5° C., then the mixture is allowed to return to AT and stirring is maintained for 1 hour. 1 ml of concentrated HCl is added and then extraction is carried out with DCM. The organic phase is washed with a 10% NaOH solution and then with an NaCl solution. 15.1 g of the expected compound are obtained.

B) (7-Ethyl-2-methyl-1H-indol-3-yl)(2,3-dichlorophenyl)methanone.

14.2 ml of 3M of MeMgI in $Et_2O$ are placed under argon and 6.78 g of 7-ethyl-2-methyl-1H-indole in 40 ml of $Et_2O$ are added dropwise. After 30 minutes, 17.84 g of 2,3-dichlorobenzoyl chloride in 60 ml of $Et_2O$ are added dropwise and the reaction medium is left stirring for 2 hours. The reaction medium is run quickly onto a saturated $NH_4Cl$ solution. The extraction is carried out with $Et_2O$ (twice) and then the organic phase is washed with a 10% NaOH solution, water and then a saturated NaCl solution. 5.5 g of the expected compound are obtained.

C) 3-(3-(2,3-Dichlorobenzoyl)-7-ethyl-2-methyl-1H-indol-1-yl)-N,N-dimethyl-1-propanesulphonamide.

A mixture comprising 1.5 g of the compound of the preceding stage, 3.34 g of the compound of stage A and 0.15 g of TDA-1 is prepared, 1.7 g of crushed sodium hydroxide are added and the mixture is heated at reflux for 36 hours. The reaction medium is cooled and then it is poured onto water. Extraction is carried out with toluene and then the extract is washed with water and then with a saturated NaCl solution. The extract is dried and evaporated and then the residue is chromatographed on silica while eluting with an AcOEt/cyclohexane (1/1, v/v) mixture. The product obtained crystallizes from an AcOEt/cyclohexane (3/7, v/v) mixture. 0.7 g of the expected compound is obtained, M.p.=18° C.

NMR:δ (ppm):1.1:t:3H; 2:mt:2H; 2.4:s:3H; 2.8:s:6H; 2.9:mt:2H; 3.2:mt:2H; 4.4:t:2H; 6.8 to 7.2:m:3H; 7.3 to 7.6:dd+t:7.8:dd:1H.

The intermediates of formula (IV) described below are prepared by using process A:

TABLE 2

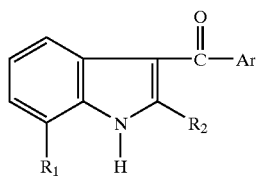

(IV)

| Preparations | $R_1$ | $R_2$ | Ar | M.p. (° C.)/NMR:δ (ppm) |
|---|---|---|---|---|
| 2.1 | Cl | Me | 2,3-dichlorophenyl | 2.2:s:3H; 7:t:1H; 7.1 to 7.5:m:4H; 7.7:d:1H; 12.3:bs:1H. |
| 2.2 | Cl | Me | 2-Me-3-Cl-phenyl | 2.2:s:3H; 2.4:s:3H; 7.0:t:1H; 7.2 to 7.6:m:4H; 7.6:dd:1H; 12.4:bs:1H. |
| 2.3 | Cl | Me | 2-F-3-$CF_3$-phenyl | 2.4:s:3H; 7.2:t:1H; 7.3:d:1H; 7.4:d:1H; 7.7:mt:2H; 7.9:t:1H; 8:t:1H; 12.6:s:1H. |
| 2.4 | Cl | Me | 2-Br-3-Me-phenyl | 2.2:s:3H; 2.4:s:3H; 7.0:t:1H; 7.2:m:2H; 7.3 to 7.6:m:3H. |
| 2.5 | Cl | Me | 2-Me-3-MeO-phenyl | 2:s:3H; 2.4:s:3H; 4:s:3H; 6.9:d:1H; 7.2:t + d:2H; 7.4:m:3H; 12.4:bs:1H. |
| 2.6 | Pr | Me | 2-Cl-3-$NO_2$-phenyl | 0.9:t:3H; 1.6:q:2H; 2.2:s:3H; 2.8:t:2H; 6.9:mt:2H; 7.2:mt:1H; 7.7:mt:2H; 8.2:mt:1H; 12:bs:1H. |

TABLE 2-continued

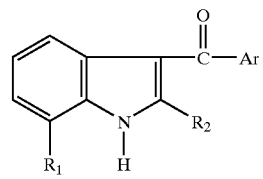

(IV)

| Preparations | $R_1$ | $R_2$ | Ar | M.p. (° C.)/NMR:δ (ppm) |
|---|---|---|---|---|
| 2.7 | iPr | Me | 2,3-dichlorophenyl | 1 to 1.4:d:6H; 3.2:mt:1H; 7 to 8:m:6H; 12:bs:1H. |
| 2.8 | Br | Me | 2,3-dichlorophenyl | 2.4:s:3H; 7.0:t:1H; 7.5:mt:3H; 7.6:t:1H; 7.9:dd:1H; 12.3:s:1H. |
| 2.9 | Et | Me | 2,3-dichlorophenyl | 1.3:t:3H; 2.4:s:3H; 2.9:q:2H; 7.0:mt:2H; 7.2:mt:1H; 7.4:dd:1H; 7.6:t:1H; 7.9:dd:1H; 12:bs:1H. |
| 2.10 | Br | Me | 2-Cl-3-$NO_2$-phenyl | 2:s:3H; 7:t:1H; 7.5:mt:2H; 7.8:mt:2H; 8.2:dd:1H; 12.4:bs:1H. |
| 2.11 | OMe | Me | 1-(4-bromonaphthyl) | 120° C. |

The intermediates of formula (XII) described below are prepared by using process B or process $B_1$:

TABLE 3

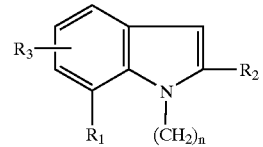

(XII)

| Preparations | $R_1$ | $R_2$ | $R_3$ | n | Y | NMR/M.p. (° C.) | Process |
|---|---|---|---|---|---|---|---|
| 3.1 | Br | Me | H | 2 | Set | NMR | B |
| 3.2 | Cl | Me | H | 2 | Set | NMR | B |
| 3.3 | Cl | Me | H | 3 | $NHSO_2Me$ | NMR | $B_1$ |
| 3.4 | Et | Me | H | 3 | $NHSO_2Me$ | NMR | $B_1$ |
| 3.5 | Br | Me | H | 3 | $NHSO_2Me$ | NMR | $B_1$ |
| 3.6 | Et | H | H | 4 | $NHSO_2Me$ | NMR | $B_1$ |
| 3.7 | OMe | Me | H | 2 | Ome | NMR | B |
| 3.8 | Br | Me | H | 2 | OEt | NMR | B |
| 3.9 | Cl | Et | H | 3 | $NHSO_2Me$ | 98° C. | $B_1$ |
| 3.10 | Cl | Me | 6-Cl | 3 | $NHSO_2Me$ | NMR | $B_1$ |
| 3.11 | OMe | Me | 6-Cl | 3 | $NHSO_2Me$ | NMR | $B_1$ |
| 3.12 | Cl | Me | 6-Me | 3 | $NHSO_2Me$ | NMR | $B_1$ |
| 3.13 | Cl | Me | H | 2 | $NHSO_2NMe_2$ | NMR | $B_1$ |
| 3.14 | Cl | Me | H | 3 | $NHSO_2NMe_2$ | 81° C. | $B_1$ |
| 3.15 | Cl | Me | H | 3 | $NHSO_2Et$ | 82° C. | $B_1$ |
| 3.16 | Cl | Me | 6-Cl | 3 | $NHSO_2Et$ | 69° C. | $B_1$ |
| 3.17 | Me | Me | 6-Cl | 3 | $NHSO_2Me$ | NMR | $B_1$ |
| 3.18 | Cl | Me | 6-Cl | 3 | $NHSO_2CF_3$ | NMR | $B_1$ |
| 3.19 | Cl | Me | H | 3 | $NHSO_2CF_3$ | NMR | $B_1$ |
| 3.20 | Me | Et | H | 3 | $NHSO_2Me$ | NMR | $B_1$ |
| 3.21 | Br | Et | H | 3 | $SO_2NMe_2$ | NMR | $B_1$ |
| 3.22 | H | Me | H | 3 | $NHSO_2Me$ | NMR | $B_1$ |

TABLE 3-continued

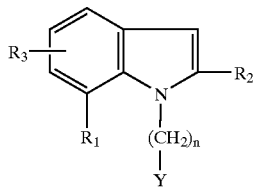

(XII)

| Preparations | R₁ | R₂ | R₃ | n | Y | NMR/M.p. (° C.) | Process |
|---|---|---|---|---|---|---|---|
| 3.23 | Br | Me | H | 3 | NHSO₂NMe₂ | NMR | B₁ |
| 3.24 | Br | Me | 6-Me | 3 | NHSO₂Me | 73° C. | B₁ |

Preparation 3.1: NMR:δ (ppm):1:t:3H; 2.4:s:3H; 2.5:mt:2H; 2.8:mt:2H; 4.5:mt:2H; 6.2:s:1H; 6.8:mt:1H; 7.2:d:1H; 7.4:d:1H.
Preparation 3.2: NMR:δ (ppm):1.25:t:3H; 2.4 to 2.8:m:5H; 3:t:2H; 4.8:t:2H; 7 to 8.2:m:6H.
Preparation 3.3: NMR:δ (ppm):1.8:qt:2H; 2.4:s:3H; 2.9:s:3H; 3.0:t:2H; 4.4:t:2H; 6.2:s:1H ; 6.9:t:1H; 7:mt:2H; 7.4:dd:1H.
Preparation 3.4: NMR:δ (ppm):1.2:t:3H; 1.7:t:2H; 2.2:s:3H; 2.9:s + mt:7H; 4.2:t:2H; 6.2:s:1H; 6.9:m:2H; 7.1:t:1H; 7.2:dd:1H.
Preparation 3.5: NMR:δ (ppm):1.8:mt:2H; 2.4:s:3H; 2.8:s:3H; 3.0:qt:2H; 4.4:t:2H; 6.2:s:1H; 6.8:t:1H; 7.0:t:1H; 7.2 and 7.4:dd:2H.
Preparation 3.6: NMR:δ (ppm):1.2:t:3H; 1.2 to 2:2mt:4H; 3:mt:4H; 4.3:t:2H; 6.4:d:1H; 7:m:4H; 7.4:2mt:2H.
Preparation 3.7: NMR:δ (ppm):2.4:s:3H; 3.1:s:3H; 3.5:t:2H; 3.8:s:3H; 4.4:t:2H; 6.1:s:1H; 6.5:d:1H; 6.8:t:1H; 7.0:d:1H.
Preparation 3.8: NMR:δ (ppm):1:t:3H; 2.4:s:3H; 3.3:q:2H; 3.6:t:2H; 4.5:t:2H; 6.2:s:1H; 6.8:t:1H; 7.2:d:1H; 7.4:d:1H.
Preparation 3.10: NMR:δ (ppm):1.85:qt:2H; 2.40:s:3H; 2.90:s:3H; 3:q:2H; 4.5:t:2H; 6.3:s:1H; 7 to 7.5:m:3H.
Preparation 3.11: NMR:δ (ppm):1.85:qt:2H; 2.40:s:3H; 2.90:s:3H; 3:q:2H; 3.95:s:3H; 4.3:t:2H; 6.3:s:1H; 7:d:1H; 7.1:t:1H; 7.2:d:1H.
Preparation 3.12: NMR:δ (ppm):1.85:qt:2H; 2.40:s:6H; 2.90:s:3H; 3:q:2H; 4.5:t:2H; 6.3:s:1H; 7 to 7.5:m:3H.

TABLE 3-continued

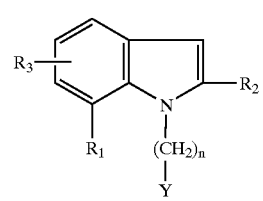

(XII)

| Preparations | R₁ | R₂ | R₃ | n | Y | NMR/M.p. (° C.) | Process |
|---|---|---|---|---|---|---|---|

Preparation 3.13: NMR:δ (ppm):2.40:s:3H; 2.55:s:6H; 3.2:q:2H; 4.5:t:2H; 6.3:s:1H; 6.8 to 7.6:m:4H.
Preparation 3.17: NMR:δ (ppm):1.80:qt:2H; 2.40:s:3H; 2.70:s:3H; 2.90:s:3H; 3.00:q:2H; 4.30:t:2H; 6.20:s:1H; 7.00:d:1H; 7.10:t:1H; 7.25:d:1H.
Preparation 3.18: NMR:δ (ppm):1.80:qt:2H; 2.30:s:3H; 3.20:t:2H; 4.35:t:2H; 6.25:s:1H; 7.10:d:1H; 7.35:d:1H; 9.50:bs:1H.
Preparation 3.19: NMR:δ (ppm):1.85:qt:2H; 2.35:s:3H; 3.20:t:2H; 4.40:t:2H; 6.25:s:1H; 6.85:t:1H; 7.00:d:1H; 7.35:d:1H; 9.50:bs:1H.
Preparation 3.20: NMR:δ (ppm):1.20:t:3H; 1.80:mt:2H; 2.65:q:2H; 2.80:s:3H; 2.95:mt:2H; 4.40:t:2H; 6.20:s:1H; 6.80:t:1H; 7.00:s:1H; 7.20:d:1H; 7.40:d:1H.
Preparation 3.21: NMR:δ (ppm):1.30:t:3H; 2.10:mt:2H; 2.60 to 3.40:m:10H; 4.50:t:2H; 6.30:s:1H; 6.90:t:1H; 7.20 to 7.60:m:2H.
Preparation 3.22: NMR:δ (ppm):1.85:qt:2H; 2.40:s:3H; 2.90:s:3H; 3.00:q:2H; 4.15:t:2H; 6.20:s:1H; 6.80 to 7.60:m:5H.
Preparation 3.23: NMR:δ (ppm):1.80:qt:2H; 2.35:s:3H; 2.60:s:6H; 2.90:q:2H; 4.40:t:2H; 6.25:s:1H; 6.80:t:1H; 7 to 7.50:m:4H.

By carrying out the preparation according to one of the processes described, the compounds according to the invention collated in the table below were prepared:

TABLE 4

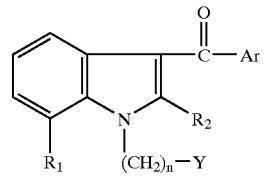

(I)

| Examples | R₁ | R₂ | n | Y | Ar | M.p. (° C.)/NMR | Process |
|---|---|---|---|---|---|---|---|
| 11 | Cl | Me | 3 | SEt | 2,3-dichlorophenyl | NMR | A₁ |
| 12 | Cl | Me | 3 | SMe | 2-F-3-CF₃-phenyl | 81° C. | A₁ |
| 13 | Cl | Me | 3 | SO₂Me | 2-F-3-CF₃-phenyl | 166° C. | A₂ |
| 14 | Cl | Me | 3 | SO₂Et | 2,3-dichlorophenyl | 61° C. | A₂ |
| 15 | Cl | Me | 2 | SEt | 2,3-dichlorophenyl | 100° C. | A |
| 16 | Cl | Me | 2 | SO₂Et | 2,3-dichlorophenyl | 119° C. | A₂ |
| 17 | Cl | Me | 3 | SMe | 2-Cl-3-NO₂-phenyl | 95° C. | B₁ |
| 18 | Cl | Me | 3 | SO₂Me | 2-Cl-3-NO₂-phenyl | 149° C. | A₂ |
| 19 | Cl | Me | 3 | SMe | 2-Br-3-Me-phenyl | 95° C. | A₁ |
| 20 | Cl | Me | 3 | SMe | 2-Me-3-Cl-phenyl | NMR | A₁ |
| 21 | Cl | Me | 3 | SO₂Me | 2-Me-3-OMe-phenyl | 140° C. | A₂ |
| 22 | Cl | Me | 3 | NHSO₂Me | 2,3-dichlorophenyl | 125° C. | A₁ |
| 23 | Cl | Me | 3 | SO₂Me | 2-Me-3-Cl-phenyl | 147° C. | A₂ |
| 24 | Cl | Me | 3 | SMe | 2-NO₂-3-Cl-phenyl | 132° C. | B₁ |
| 25 | Cl | Me | 3 | SMe | 2-Me-3-OMe-phenyl | 56° C. | A₁ |
| 26 | Cl | Me | 4 | SMe | 2,3-dichlorophenyl | 99° C. | B₁ |
| 27 | Cl | Me | 3 | SMe | 2-SMe-3-NO₂-phenyl | NMR | B₁ |
| 28 | Cl | Me | 4 | SMe | 2-F-3-CF₃-phenyl | 86–87° C. | B₁ |
| 29 | Cl | Me | 4 | SO₂Me | 2,3-dichlorophenyl | 115° C. | A₂ |
| 30 | Cl | Me | 4 | SO₂Me | 2-F-3-CF₃-phenyl | 183° C. | A₂ |
| 31 | Cl | Me | 3 | SMe | 2-Me-4-Br-phenyl | 60–61° C. | B₁ |
| 32 | Cl | Me | 3 | SO₂Me | 2-Me-4-Br-phenyl | 154–155° C. | A₂ |
| 33 | Cl | Me | 3 | NHSO₂Me | 2-Cl-3-NO₂-phenyl | NMR | B₁ |

TABLE 4-continued

Structure (I): indole with 3-C(=O)-Ar, 2-$R_2$, 7-$R_1$, N-$(CH_2)_n$-Y

| Examples | $R_1$ | $R_2$ | n | Y | Ar | M.p. (° C.)/ NMR | Process |
|---|---|---|---|---|---|---|---|
| 34 | Cl | Me | 2 | SEt | 2-F-3-$CF_3$-phenyl | NMR | B |
| 35 | Cl | Me | 2 | $SO_2Et$ | 2-F-3-$CF_3$-phenyl | 187° C. NMR | $A_2$ |
| 36 | Cl | Me | 2 | $SO_2Et$ | 2-Cl-3-$NO_2$-phenyl | 128° C. | $A_2$ |
| 37 | Cl | Me | 3 | $NHSO_2Me$ | 2-$NO_2$-3-Cl-phenyl | 105° C. | $B_1$ |
| 38 | Cl | Me | 2 | SEt | 2-Cl-3-$NO_2$-phenyl | NMR | B |
| 39 | Cl | Me | 3 | SOMe | 2,3-dichlorophenyl | NMR | $A_2$ |
| 40 | Cl | Me | 3 | OMe | 2,3-dichlorophenyl | 110° C. | $A_1$ |
| 41 | iPr | Me | 3 | SMe | 2,3-dichlorophenyl | 113° C. | A |
| 42 | iPr | Me | 2 | $SO_2Et$ | 2,3-dichlorophenyl | 131° C. | $A_2$ |
| 43 | iPr | Me | 3 | $SO_2Me$ | 2,3-dichlorophenyl | 159° C. | $A_2$ |
| 44 | Br | Me | 2 | SEt | 2,3-dichlorophenyl | 100° C. | A |
| 45 | Br | Me | 2 | $SO_2Et$ | 2,3-dichlorophenyl | 157° C. | $A_2$ |
| 46 | Br | Me | 3 | $NHSO_2Me$ | 2,3-dichlorophenyl | 147° C. | $A_1$ |
| 47 | Br | Me | 2 | SEt | 2-F-3-$CF_3$-phenyl | 126° C. | B |
| 48 | Br | Me | 2 | SEt | 2-Cl-3-$NO_2$-phenyl | 100° C. | A |
| 49 | Br | Me | 2 | $SO_2Et$ | 2-F-3-$CF_3$-phenyl | 180° C. | $A_2$ |
| 50 | Br | Me | 3 | $NHSO_2Me$ | 2-F-3-$CF_3$-phenyl | 173° C. NMR | $B_1$ |
| 51 | Br | Me | 3 | $NHSO_2Me$ | 2-$NO_2$-3-Cl-phenyl | 101° C. | $B_1$ |
| 52 | Br | Me | 4 | OMe | 2-F-3-$CF_3$-phenyl | 75° C. | $A_1$ |
| 53 | Br | Me | 2 | OEt | 2,3-dichlorophenyl | 135° C. | B |
| 54 | Et | H | 3 | SMe | 2,3-dichlorophenyl | 84° C. | $B_1$ |
| 55 | Et | H | 3 | $SO_2Me$ | 2,3-dichlorophenyl | 90° C. | $A_2$ |
| 56 | Et | H | 3 | SMe | 2-Cl-3-$NO_2$-phenyl | NMR | $B_1$ |
| 57 | Et | H | 3 | $SO_2Me$ | 2-Cl-3-$NO_2$-phenyl | 79° C. | $A_2$ |
| 58 | Et | H | 4 | SMe | 2-SMe-3-$NO_2$-phenyl | 93° C. | $A_1$ |
| 59 | Et | H | 4 | $SO_2Me$ | 2-$SO_2Me$-3-$NO_2$-phenyl | 109° C. | $A_2$ |
| 60 | Et | H | 3 | $SO_2Me$ | 2-SMe-3-$NO_2$-phenyl | 73° C. | $A_2$ |
| 61 | Et | H | 4 | $SO_2Me$ | 2-OEt-3-$NO_2$-phenyl | 63° C. | $A_2$ |
| 62 | Et | H | 4 | $NHSO_2Me$ | 2,3-dichlorophenyl | 65° C. | $B_1$ |
| 63 | Et | Me | 2 | SEt | 2,3-dichlorophenyl | 87° C. | A |
| 64 | Et | Me | 2 | $SO_2Et$ | 2,3-dichlorophenyl | 171° C. | $A_2$ |
| 65 | Et | Me | 3 | $NHSO_2Me$ | 2,3-dichlorophenyl | 82° C. | $A_1$ |
| 66 | Et | Me | 3 | $SO_2Me$ | 2,3-dichlorophenyl | 125° C. | $A_2$ |
| 67 | Et | Me | 3 | $NHSO_2Me$ | 2-F-3-$CF_3$-phenyl | 144° C. | $B_1$ |
| 68 | Et | Et | 3 | $NMeSO_2Me$ | 2-F-3-$CF_3$-phenyl | NMR | $A_3$ |
| 69 | nPr | Me | 3 | $NHSO_2Me$ | 2-Cl-3-$NO_2$-phenyl | NMR | $A_1$ |
| 70 | OMe | Me | 2 | OMe | 1-(4-bromonaphthyl) | 152° C. | B |
| 71 | OMe | Me | 2 | OMe | 2,3-dichlorophenyl | 120° C. | A |

Example 11: NMR:δ (ppm):1.1:t:3H ; 1.9:mt:2H; 2.4:s:3H; 2.5 to 2.7:mt:4H; 4.6:t:2H; 7.1:t:1H; 7.2 to 7.6:m:4H; 7.8:dd:1H.
Example 20: NMR:δ (ppm):1.85 to 2.2:m:5H; 2.3 to 2.8:m:8H; 4.6:t:2H; 7 to 7.6:m:6H.
Example 27: NMR:δ (ppm):1.8 to 2.8:m:13H; 4.6:t:2H; 6.8 to 8.2:m:6H.
Example 33: NMR:δ (ppm):2:mt 2H; 2.4:s:3H; 2.9:s:3H; 3.1:q:2H; 4.6:mt:2H; 7 to 8.1:m:7H.
Example 34: NMR:δ (ppm):1.25:t:3H; 2.4 to 2.8:m:5H; 3:t:2H; 4.8:t:2H; 7 to 8.2:m:6H.
Example 35: NMR:δ (ppm):1.1:t:3H; 2.5:s:3H; 3.2:q:2H; 3.6:t:2H; 4.9:t:2H; 7:t:1H; 7.3:mt:2H; 7.5:t:1H; 7.8:t:1H.
Example 38: NMR:δ (ppm):1.1:t:3H; 2.3 to 6:s + mt:5H; 2.9:t:2H; 4.7:t:2H; 7:t:1H; 7.2:dd:1H; 7.3:dd:1H; 7.7:m:2H; 8.2:mt:1H.
Example 39: NMR:δ (ppm):2.1:mt:2H; 2.4 to 2.6:2s:6H; 2.8:mt:2H; 4.7:mt:2H; 7.1:t:1H; 7.2 to 7.6:m:4H; 7.9:dd:1H.
Example 50: NMR:δ (ppm):1.25:t:3H; 2.45:s:3H; 3.05:q:2H; 3.7:t:2H; 5:t:2H; 7 to 8.4:m:6H.
Example 56: NMR:δ (ppm):1.25:t:3H; 1.8 to 2.15:m:5H; 2.4:t:2H; 4.35:t:2H; 7 to 8.2:m:2H.
Example 68: NMR:δ (ppm):1 to 1.4:2t:6H; 1.8 to 2:mt:2H; 2.7 to 3.1:m + 2s:10H; 3.2:t:2H; 4.3:t:2H; 6.9:m:3H; 7.5:t:1H; 7.8:t:1H; 8:t:1H.
Example 69: NMR:δ (ppm):1:t:3H; 1.6:mt:2H; 1.8:mt:2H; 2.4:s:3H; 2.8 to 3.2:m:7H; 4.3:mt:2H; 6.9 to 8.3:m:7H.

EXAMPLE 72

(Process B)

N-(3-(6,7-Dichloro-3-[2-fluoro-3-(trifluoromethyl)benzoyl]-2-methyl-1H-indol-1-yl)propyl)methanesulphonamide I: $R_1=R_3=Cl$, $R_2=Me$, $R'_3=H$, $Ar=2$-F-3-$CF_3$-phenyl, $Y=$—$NHSO_2Me$, $A=(CH_2)_n$, $n=3$.

A) 6,7-Dichloro-1-(3-chloropropyl)-2-methyl-1H-indole.

7.84 g of crushed sodium hydroxide, 190 ml of toluene, 7 g of 6,7-dichloro-2-methyl-1H-indole, 85 ml of toluene and 0.7 g of tetrabutylammonium hydrogensulphate are introduced under nitrogen. The mixture is heated at reflux for 30 minutes, then 14 ml of 1-bromo-3-chloropropane are added and reflux is maintained for 2 hours. The reaction medium is poured onto water and the aqueous phase is washed with toluene. Extraction is carried out with toluene and then the extract is washed with water and with a saturated NaCl solution. The extract is dried and evaporated to produce 11.3 g of the expected compound.

B) 6,7-Dichloro-1-(3-iodopropyl)-2-methyl-1H-indole.

11.3 g of the compound of the preceding stage are introduced into 520 ml of acetonitrile and 43 g of NaI, and then the mixture is heated at reflux for 3 days. The reaction medium is poured onto water and is diluted with toluene and then the aqueous phase is washed twice with toluene. The organic phases are combined and then washed with water and then with a saturated NaCl solution. They are dried and concentrated to produce 13.93 g of the expected compound.

C) N-[3-(6,7-Dichloro-2-methyl-1H-indol-1-yl)propyl]methanesulphonamide.

6.04 g of 60% NaH are introduced under nitrogen into 400 ml of anhydrous DMF. The mixture is cooled to 5° C. and then 14.35 g of methanesulphonamide in 200 ml of anhydrous DMF are added. After stirring for 10 minutes at 5° C., 13.9 g of the compound obtained in the preceding stage in 200 ml of anhydrous DMF are added and the mixture is allowed to return to AT. After stirring for 3 hours, the reaction medium is poured onto water and is then diluted with DCM. The aqueous phase is washed 3 times with DCM and then the organic phases are combined. They are washed with water and with a saturated NaCl solution. They are dried and concentrated and then the residue is chromatographed on silica while eluting with a cyclohexane/AcOEt (50/50, v/v) mixture. 7.43 g of the expected compound are obtained.

NMR:δ (ppm):1.80:mt:2H; 2.35:s:3H; 2.60:s:6H; 2.90:mt:2H; 4.40:t:2H; 6.30:s:1H; 7.10:d:1H; 7.20:mt:1H; 7.35:d:1H.

D) N-(3-(6,7-Dichloro-3-[2-fluoro-3-(trifluoromethyl)benzoyl]-2-methyl-1H-indol-1-yl)propyl)methanesulphonamide 1 g of the compound of the preceding stage and 1.35 g of 2-fluoro-3-(trifluoromethyl)benzoyl chloride are introduced into 120 ml of DCM. The mixture is cooled to between −20° C. and −25° C., and 3.3 ml of dichloroethylaluminium are added using a syringe. The mixture is allowed to return to ambient temperature and is kept stirred for 3 hours. The reaction medium is poured onto water, the aqueous phase is washed 3 times with DCM and then the organic phases are combined and filtered through Celite®. The combined organic phases are washed with a 10% NaOH solution, water, a 10% HCl solution and then a saturated NaCl solution. 0.94 g of the expected compound is obtained, which compound crystallizes from ether, M.p.=181° C.

EXAMPLE 73

(Process B)

N-(2-(7-Chloro-3-(2,3-dichlorobenzoyl)-2-methyl-1H-indol-1-yl)ethyl)-N,N-dimethylsulphamide I: $R_1=7$-Cl, $R_2=Me$, $R_3=R'_3=H$, $Y=NHSO_2Me_2$, $A=(CH_2)_n$, $n=2$, $Ar=2,3$-dichlorophenyl.

A) 3-(7-Chloro-2-methyl-1H-indol-1-yl)propanenitrile.

20 g of 7-chloro-2-methyl-1H-indole are mixed in 100 ml of dioxane with 3 g of triton B, 3 g of acrylonitrile are slowly added, 250 ml of dioxane are added again and then the mixture is heated at 60° C. for 2 hours. The medium is evaporated and then the residue is taken up in AcOEt. The precipitate formed being removed, the product obtained is used as is in the following stage.

B) 3-(7-Chloro-2-methyl-1H-indol-1-yl)propanoic acid

A solution of 35 g of KOH in 350 ml of water is prepared and this solution is added to the mixture containing the product of the preceding stage in 175 ml of ethanol. The medium is heated to 80° C. and then the reaction medium is poured into 500 ml of 10% aqueous HCl solution. The extraction is carried out with DCM and then the extract is washed with a saturated NaCl solution. 22.5 g of the expected compound are obtained.

C) 2-(7-Chloro-2-methyl-1H-indol-1-yl)-1-ethanamine.

22.5 g of the compound of the preceding stage, 27.2 g of diphenylphosphoryl azide and 10 g of triethylamine are mixed in 400 ml of tert-butanol and the mixture is heated at 80° C. for 3 hours. The reaction medium is poured onto 500 ml of saturated $NaHCO_3$ solution, 500 ml of AcOEt are added and then separation by settling is carried out. The organic phase is evaporated, the residue is then taken up in a mixture of 10 ml of concentrated HCl in 500 ml of ethanol and the mixture is heated to reflux for 6 hours. The mixture is basified to pH 14 by addition of 30% sodium hydroxide and is then extracted with AcOEt, and the extract is washed with a saturated NaCl solution. 2.61 g of the expected compound are obtained.

D) N'-(2-(7-Chloro-2-methyl-1H-indol-1-yl)ethyl)-N,N-dimethylsulphamide.

2.63 g of the compound of the preceding stage are suspended under nitrogen in 20 ml of $CH_3CN$ and 2 ml of triethylamine. A solution of 2 g of dimethylsulphamoyl chloride in 20 ml of water is prepared and this solution is run onto the reaction medium, cooled to −50° C. The reaction medium is allowed to return to AT and is then heated at 50° C. for 3 hours. The reaction medium is run quickly onto a saturated $NH_4Cl$ solution and is then extracted with acetonitrile. The extract is dried and evaporated and then the residue is chromatographed on silica while eluting with an AcOEt/cyclohexane (1/1, v/v) mixture. 0.86 g of the expected compound is obtained.

NMR:δ (ppm):2.40s:3H; 2.55:s:6H; 3.2:q:2H; 4.5:t:2H; 6.3:s:1H; 6.8 to 7.6:m:4H.

E) N-(2-(7-Chloro-3-(2,3-dichlorobenzoyl)-2-methyl-1H-indol-1-yl)ethyl)-N,N-dimethylsulphamide.

0.86 g of the compound of the preceding stage and 0.75 g of 2,3-dichlorobenzoyl chloride are introduced under nitrogen into 50 ml of DCM. The mixture is cooled to −50°

C. and 4.8 ml of 1.8M dichloroethylaluminium in toluene are added at this temperature. The mixture is allowed to return to AT and is kept stirred for 3 hours. The reaction medium is run quickly onto NH$_4$Cl and is then extracted with DCM. The extract is washed with a 10% HCl solution, with a 10% NaOH solution and then with a saturated NaCl solution. The extract is dried and evaporated and the residue is chromatographed on silica while eluting with the AcOEt/cyclohexane (1/1, v/v) e. 0.49 g of the expected compound is obtained, M.p.=75° C.

TABLE 5

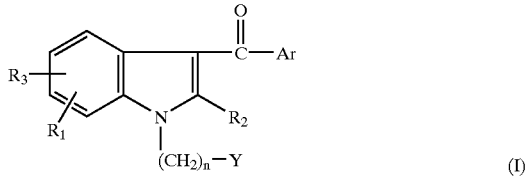

(I)

| Examples | R$_1$ | R$_2$ | R$_3$ | n | Y | Ar | M.p. (° C.)/ NMR | Process |
|---|---|---|---|---|---|---|---|---|
| 74 | 7-Br | Et | H | 3 | SO$_2$NMe$_2$ | 2-F-3-CF$_3$-phenyl | 114° C. | B$_1$ |
| 75 | 7-Br | Et | H | 3 | SO$_2$NMe$_2$ | 2,3-dichloro-phenyl | 118° C. | B$_1$ |
| 76 | 7-Br | Me | H | 3 | NHSO$_2$Me | 2-Br-3-Me-phenyl | 83° C. | B$_1$ |
| 77 | 7-Cl | Me | H | 2 | NHSO$_2$Me | 2,3-dichloro-phenyl | 140° C. | A$_1$ ? |
| 78 | 7-Br | Et | H | 3 | NHSO$_2$Me | 2-F-3-CF$_3$-phenyl | 57° C. | B$_1$ |
| 79 | 7-Br | Me | H | 3 | NHSO$_2$NMe$_2$ | 2-F-3-CF$_3$-phenyl | 158° C. | B$_1$ |
| 80 | 7-Br | Me | H | 3 | NHSO$_2$NMe$_2$ | 2,3-dichloro-phenyl | 119° C. | B$_1$ |
| 81 | 7-Et | Me | H | 3 | NMeSO$_2$Me | 2-F-3-CF$_3$-phenyl | NMR | A$_3$ |
| 82 | 7-Cl | Et | H | 3 | NMeSO$_2$Me | 2-F-3-CF$_3$-phenyl | NMR | A$_3$ |
| 83 | 7-Cl | Me | H | 2 | SOEt | 3-Cl-3-NO$_2$-phenyl | 125° C. | A$_2$ |
| 84 | 7-Cl | Et | H | 3 | NHSO$_2$Me | 2-F-3-CF$_3$-phenyl | 139° C. | B$_1$ |
| 85 | 7-Cl | Et | H | 3 | NHSO$_2$Me | 2,3-dichloro-phenyl | 85° C. | B$_1$ |
| 86 | 7-Cl | Me | H | 3 | NHSO$_2$Me | 2-Me-3-CF$_3$-phenyl | 68° C. | B$_1$ |
| 87 | 7-Cl | Me | H | 3 | NHSO$_2$Me | 2-F-3-Cl-phenyl | 189° C. | B$_1$ |
| 88 | 7-Cl | Me | H | 3 | NHSO$_2$Me | 2-Br-3-Me-phenyl | 75° C. | B$_1$ |
| 89 | 7-Cl | Me | H | 3 | NHSO$_2$Me | 4-bromo-1-naphthyl | 103° C. | B$_1$ |
| 90 | 7-Et | Me | H | 3 | NHSO$_2$Me | 2-F-3-Cl-phenyl | 127° C. | B$_1$ |
| 91 | 7-Cl | Et | H | 3 | NHSO$_2$Me | 2-Br-3-Me-phenyl | 112° C. | B$_1$ |
| 92 | 7-Cl | Et | H | 3 | NHSO$_2$Me | 2-F-3-Cl-phenyl | 71° C. | B$_1$ |
| 93 | 7-Cl | Et | H | 3 | NHSO$_2$Me | 4-bromo-1-naphthyl | 108° C. | B$_1$ |
| 94 | 7-Et | Me | H | 3 | NHSO$_2$Me | 4-bromo-1-naphthyl | 81° C. | B$_1$ |
| 95 | 7-Cl | Et | H | 3 | NHSO$_2$Me | 2-Me-3-CF$_3$-phenyl | 57° C. | B$_1$ |
| 96 | 7-Et | Me | H | 3 | NHSO$_2$Me | 2-Me-3-CF$_3$-phenyl | 144° C. | B$_1$ |
| 97 | H | Me | H | 3 | NHSO$_2$Me | 2-F-3-CF$_3$-phenyl | 133° C. | B$_1$ |
| 98 | H | Me | H | 3 | NHSO$_2$Me | 2,3-dichloro-phenyl | NMR | B$_1$ |
| 99 | H | Me | H | 3 | NHSO$_2$Me | 2-Me-3-CF$_3$-phenyl | 137° C. | B$_1$ |
| 100 | 7-Et | Me | H | 3 | NHSO$_2$Me | 2-Br-3-Me-phenyl | 88° C. | B$_1$ |
| 101 | 7-Cl | Me | 6-Cl | 3 | NHSO$_2$Me | 2,3-dichloro-phenyl | 127° C. | B$_1$ |
| 102 | 7-Cl | Me | 6-Cl | 3 | NHSO$_2$Me | 2-Me-3-CF$_3$-phenyl | 74° C. | B$_1$ |

TABLE 5-continued $$\text{(I)}$$

Structure: indole with $R_3$ on benzene ring, $R_1$ at 7-position, $N$-(CH$_2$)$_n$-Y, 2-$R_2$, 3-C(=O)-Ar

| Examples | R$_1$ | R$_2$ | R$_3$ | n | Y | Ar | M.p. (° C.)/ NMR | Process |
|---|---|---|---|---|---|---|---|---|
| 103 | 7-Cl | Me | 6-Cl | 3 | NHSO$_2$Me | 3-Br-3-Me-phenyl | 75° C. | B$_1$ |
| 104 | 7-Cl | Me | 6-Cl | 3 | NHSO$_2$Me | 2-F-3-Cl-phenyl | 132° C. | B$_1$ |
| 105 | 7-Cl | Me | 4-Cl | 3 | NHSO$_2$Me | 2-F-3-CF$_3$-phenyl | 78° C. | B$_1$ |
| 106 | 7-Cl | Me | 6-Cl | 3 | NHSO$_2$Me | 4-bromo-1-naphthyl | 182° C. | B$_1$ |
| 107 | 7-Cl | Me | 4-Cl | 3 | NHSO$_2$Me | 2,3-dichloro-phenyl | 63–67° C. | B$_1$ |
| 108 | 7-Cl | Me | 4-Me | 3 | NHSO$_2$Me | 2-F-3-CF$_3$-phenyl | 95–98° C. | B$_1$ |
| 109 | 7-Cl | Me | 4-Cl | 3 | NHSO$_2$Me | 2-Me-3-CF$_3$-phenyl | 144–146° C. | B$_1$ |
| 110 | 7-Cl | Me | 4-Me | 3 | NHSO$_2$Me | 2-Me-3-CF$_3$-phenyl | 65–75° C. | B$_1$ |
| 111 | 7-Cl | Me | 4-Me | 3 | NHSO$_2$Me | 2,3-dichloro-phenyl | 85–96° C. | B$_1$ |
| 112 | 7-Cl | Me | 4-Cl | 3 | NHSO$_2$Me | 2-Br-3-Me-phenyl | 176–179° C. | B$_1$ |
| 113 | 7-Cl | Me | 5-Cl | 3 | NHSO$_2$Me | 2,3-dichloro-phenyl | 86 | B$_1$ |
| 114 | 7-Cl | Me | 5-Cl | 3 | NHSO$_2$Me | 2-Br-3-Me-phenyl | 82° C. | B$_1$ |
| 115 | 7-Cl | Me | 4-Me | 3 | NHSO$_2$Me | 2-Br-3-Me-phenyl | 119–121° C. | B$_1$ |
| 116 | 7-Cl | Me | 4-Cl | 3 | NHSO$_2$Me | 2-F-3-Cl-phenyl | 121–123° C. | B$_1$ |
| 117 | 7-Cl | Me | 5-Cl | 3 | NHSO$_2$Me | 2-F-3-CF$_3$-phenyl | 180–185° C. | B$_1$ |
| 118 | 7-Cl | Me | 5-Cl | 3 | NHSO$_2$Me | 2-Me-3-CF$_3$-phenyl | NMR | B$_1$ |
| 119 | 7-Cl | Me | 5-Cl | 3 | NHSO$_2$Me | 2-F-3-Cl-phenyl | 155–158° C. | B$_1$ |
| 120 | 7-Cl | Me | H | 3 | NHSO$_2$Et | 2-F-3-CF$_3$-phenyl | 127–129° C. | B$_1$ |
| 121 | 7-Cl | Me | H | 3 | NHSO$_2$CF$_3$ | 2-F-3-CF$_3$-phenyl | 131–133° C. | B$_1$ |
| 122 | 7-Cl | Me | H | 3 | NHSO$_2$Et | 2,3-dichloro-phenyl | 113–115° C. | B$_1$ |
| 123 | 7-Cl | Me | H | 3 | NHSO$_2$CF$_3$ | 2,3-dichloro-phenyl | 114–115° C. | B$_1$ |
| 124 | 7-Cl | Me | 6-Cl | 3 | NHSO$_2$Et | 2-F-3-CF$_3$-phenyl | 159–162° C. | B$_1$ |
| 125 | 7-Cl | Me | 6-Cl | 3 | NHSO$_2$Et | 2,3-dichloro-phenyl | 121–126° C. | B$_1$ |
| 126 | 7-Cl | Me | 6-Cl | 3 | NHSO$_2$CF$_3$ | 2-F-3-CF$_3$-phenyl | 111–114° C. | B$_1$ |
| 127 | 7-Cl | Me | 6-Cl | 3 | NHSO$_2$CF$_3$ | 2,3-dichloro-phenyl | 159–160 | B$_1$ |
| 128 | 7-OMe | Me | 6-Cl | 3 | NHSO$_2$Me | 2-F-3-CF$_3$-phenyl | 118° C. | B$_1$ |
| 129 | 7-OMe | Me | 6-Cl | 3 | NHSO$_2$Me | 2,3-dichloro-phenyl | 118–120° C. | B$_1$ |
| 130 | 7-Cl | Me | 6-Me | 3 | NHSO$_2$Me | 2-F-3-CF$_3$-phenyl | 146° C. | B$_1$ |
| 131 | 7-Cl | Me | 6-Me | 3 | NHSO$_2$Me | 2,3-dichloro-phenyl | 145–146° C. | B$_1$ |
| 132 | 7-Me | Me | 6-Cl | 3 | NHSO$_2$Me | 2-F-3-CF$_3$-phenyl | 104–108° C. | B$_1$ |
| 133 | 7-Me | Me | 6-Cl | 3 | NHSO$_2$Me | 2,3-dichloro-phenyl | 141–144° C. | B$_1$ |
| 134 | 7-Cl | Me | H | 3 | NHSO$_2$CF$_3$ | 4-bromo-1-naphthyl | 80° C. | B$_1$ |
| 135 | 7-Cl | Me | H | 3 | NHSO$_2$CF$_3$ | 2-Me-3-CF$_3$-phenyl | 70° C. | B$_1$ |

TABLE 5-continued

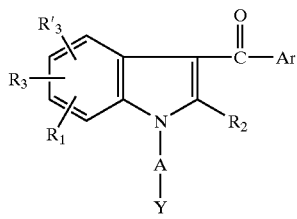

(I)

| Examples | R₁ | R₂ | R₃ | n | Y | Ar | M.p. (° C.)/ NMR | Process |
|---|---|---|---|---|---|---|---|---|
| 136 | 7-Cl | Me | H | 3 | NHSO₂NMe₂ | 2,3-dichlorophenyl | 110–113° C. | B₁ |
| 137 | 7-Cl | Me | H | 3 | NHSO₂NMe₂ | 3-F-3-CF₃-phenyl | 158–160° C. | B₁ |
| 138 | 7-Cl | Me | 6-Cl | 3 | NHSO₂NMe₂ | 2,3-dichlorophenyl | 121–123° C. | B₁ |
| 139 | 7-Cl | Me | 6-Cl | 3 | NHSO₂NMe₂ | 2-F-3-CF₃-phenyl | 148–150° C. | B₁ |
| 140 | 7-Cl | Me | 6-Me | 3 | NHSO₂NMe₂ | 2-Me-3-CF₃-phenyl | 121–124° C. | B₁ |
| 141 | 7-Cl | Me | 6-Me | 3 | NHSO₂Me | 2-F-3-Cl-phenyl | 152° C. | B₁ |
| 142 | 7-Cl | Me | 6-Me | 3 | NHSO₂Me | 4-bromo-1-naphthyl | 140–144° C. | B₁ |
| 143 | 7-Cl | Me | 6-Me | 3 | NHSO₂Me | 2-Br-3-Me-phenyl | 123–126° C. | B₁ |
| 144 | 7-F | Me | H | 3 | NHSO₂Me | 2-F-3-CF₃-phenyl | 144–150° C. | B₁ |
| 145 | 7-F | Me | H | 3 | NHSO₂Me | 2,3-dichlorophenyl | 54–60° C. | B₁ |
| 146 | 7-Br | Me | 6-Me | 3 | NHSO₂Me | 2-F-3-CF₃-phenyl | 155–158° C. | B₁ |
| 147 | 7-Cl | Me | H | 3 | NHSO₂Me | 2-F-4-CF₃-phenyl | 150–154° C. | A₁ |
| 148 | 7-Br | Me | 6-Me | 3 | NHSO₂Me | 2,3-dichlorophenyl | 167–169° C. | B₁ |

Example 81: NMR:δ (ppm):1.25:t:3H; 1.95:mt:2H; 2.50:s:3H; 2.80:s:3H; 2.90:s:3H; 3.05:q: 2H; 3.20:t:2H; 4.35:t:2H; 6.90 to 8.00:m:6H.
Example 82: NMR:δ (ppm):1.15:t:3H; 2.00:mt:2H; 2.80:s:3H; 2.85 to 3.10:m:5H; 3.25:t:2H; 4.55:1:2H; 6.90 to 8.10:m:6H.
Example 98: NMR:δ (ppm):1.9:qt:2H; 2.50:s:3H; 2.90:s:3H; 3.05:q:2H; 4.30:t:2H; 7.00 to 7.90:m:7H.
Example 118: NMR:δ (ppm):1.9:mt:2H; 2.20:m:6H; 2.85:s:3H; 3.00:q:2H; 4.50:mt:2H; 7.05:t:1H; 7.20 to 8.20:m:5H.

The invention claimed is:

1. A compound of formula:

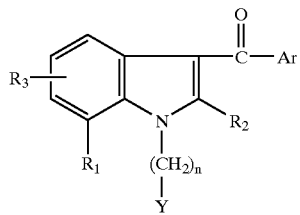

(I)

in which:

Ar represents:
  a) a phenyl mono-, di- or trisubstituted by one or more groups chosen from: a halogen atom, a (C₁–C₄)alkyl, a trifluoromethyl, an amino, a nitro, a hydroxyl, a (C₁–C₄)alkoxy, a (C₁–C₄)alkylsulphanyl or a (C₁–C₄)alkylsulphonyl;
  b) a naphthyl which is unsubstituted or substituted once or twice by a halogen atom, a (C₁–C₄)alkyl or a trifluoromethyl;

A represents a C₂–C₆ alkylene radical;
Y represents a group chosen from SR₄, SOR₄, SO₂R₄, SO₂NR₅R₆, N(R₇)SO₂R₄, OR₄ or NR₇SO₂NR₅R₆;
R₁, R₃ and R'₃ represent, each independently of one another, hydrogen, a hydroxyl, a halogen atom, a (C₁–C₄)alkyl, a trifluoromethyl or a (C₁–C₄)alkoxy;
R₂ represents hydrogen or a (C₁–C₄)alkyl;
R₄ represents a (C₁–C₄)alkyl or a trifluoromethyl;
R₅ and R₆ each independently represent hydrogen or a (C₁–C₄)alkyl;
R₇ represents hydrogen or a (C₁–C₄)alkyl;
and its optional salts and/or its solvates.

2. A compound according to claim 1 of formula:

(I)

in which:

Ar represents:
  a) a phenyl mono-, di- or trisubstituted by one or more groups chosen from: a halogen atom, a ($C_1$–$C_4$)alkyl, a trifluoromethyl, an amino, a nitro, a ($C_1$–$C_4$)alkoxy, a ($C_1$–$C_4$)alkylsulphanyl or a ($C_1$–$C_4$)alkylsulphonyl;
  b) a naphthyl which is unsubstituted or substituted once or twice by a halogen atom, a ($C_1$–$C_4$)alkyl or a trifluoromethyl;

n represents 2, 3 or 4;

Y represents a group chosen from $SR_4$, $SOR_4$, $SO_2R_4$, $SO_2NR_5R_6$, $N(R_7)SO_2R_4$ or $OR_4$;

$R_1$ represents a halogen atom, a ($C_1$–$C_4$)alkyl, a trifluoromethyl or a ($C_1$–$C_4$)alkoxy;

$R_2$ represents hydrogen or a ($C_1$–$C_4$)alkyl;

$R_3$ represents hydrogen, a ($C_1$–$C_4$)alkyl or a halogen;

$R_4$ represents a ($C_1$–$C_4$)alkyl;

$R_5$ and $R_6$ each independently represent hydrogen or a ($C_1$–$C_4$)alkyl;

$R_7$ represents hydrogen or a ($C_1$–$C_4$)alkyl;

and its optional salts and/or its solvates.

3. A compound according to claim 1 of formula (I) in which $R_1$ is in the 7 position of the indole nucleus and represents a methyl or a chlorine or bromine atom.

4. A compound according to claim 1 of formula (I) in which $R_2$ represents a ($C_1$–$C_4$)alkyl.

5. A compound according to claim 1 of formula (I) in which $R_3$ is hydrogen or $R_3$ is in the 6 position of the indole nucleus and represents either a chlorine atom or a methyl.

6. A compound according to claim 1 of formula (I) in which $R'_3$ is hydrogen.

7. A compound according to claim 1 of formula (I) in which Ar represents a phenyl mono- or disubstituted by a halogen atom, a methyl, a trifluoromethyl, a methoxy, a methylsulphanyl or a methylsulphonyl.

8. A compound according to claim 1 of formula (I) in which Y represents $SO_2R_4$ or $NHSO_2R_4$.

9. A compound according to claim 1 of formula (I) in which:
  Ar represents a phenyl mono- or disubstituted by a halogen atom, a methyl, a trifluoromethyl, a methoxy, a methylsulphanyl or a methylsulphonyl;
  A represents a $(CH_2)_n$ group;
  n represents 2, 3 or 4;
  Y represents $SO_2R_4$ or $NHSO_2R_4$;
  $R_1$ represents a methyl or a chlorine or bromine atom in the 7 position of the indole nucleus;
  $R_2$ represents a methyl;
  $R_3$ is hydrogen or $R_3$ represents either a chlorine atom or a methyl in the 6 position of the indole nucleus;
  $R'_3$ is hydrogen;
  $R_4$ represents a methyl or an ethyl;
  and its optional salts and/or its solvates.

10. Process for the preparation of a compound of formula (I) according to claim 1, of its optional salts and/or its solvates wherein:

a) an indole of formula:

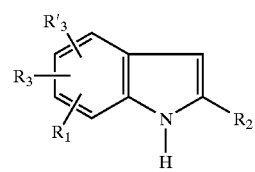

(II)

in which $R_1$, $R_2$, $R_3$ and $R'_3$ are as defined in claim 1 for a compound of formula (I), is treated with a methylmagnesium halide and with an acid halide of formula ArCOHal (III), in which Ar is as defined for the compound of formula (I) and Hal represents a halogen atom;

b) the compound thus obtained, of formula:

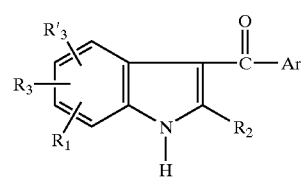

(IV)

is treated with a halide of formula Hal—A—Y (V), in which —A— and Y are as defined for a compound of formula (I) in claim 1 and Hal represents a halogen atom, in the presence of a base.

11. Process according to claim 10 wherein stage b) is modified in the following way:

b1) the compound obtained in stage a), of formula:

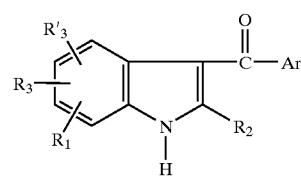

(IV)

is treated with a compound of formula Z—A—Cl (VI), in which Z represents either a hydroxyl group or a halogen atom;

b2) optionally, the compound thus obtained, of formula:

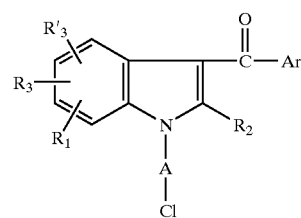

(VII)

is treated with sodium iodide;

b3) the compound thus obtained in stage b1, of formula (VII), or in stage b2), of formula:

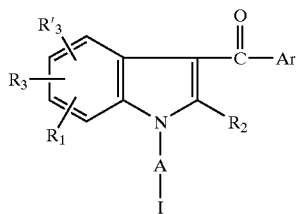

is treated with a Y anion.

12. Process according to claim 10 for preparing a compound of formula (I) in which Y represents an $SOR_4$ group or an $SO_2R_4$ group, from a compound of formula (I) in which Y represents an $SR_4$ group wherein the following additional stage is carried out:

c1) the compound obtained, of formula:

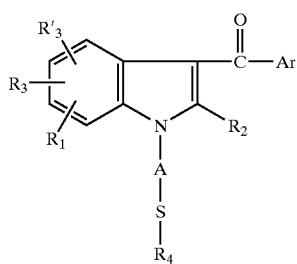

is treated with an oxidizing agent.

13. Process according to claim 10 for preparing a compound of formula (I) in which Y represents an $N(R_7)SO_2R_4$ group with $R_7$ other than H, from a compound of formula (I) in which Y represents an $NHSO_2R_4$ group wherein the following additional stage is carried out:

c2) the compound obtained, of formula:

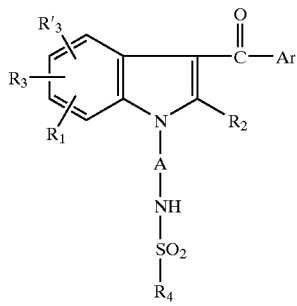

is treated with an alkylating agent in the presence of a base.

14. Process according to claim 10 for preparing a compound of formula (I) in which Y represents an $SO_2NR_5R_6$ group from a compound of formula (I) in which Y represents an $SO_2NHR_5$ group wherein the following additional stage is carried out:

c3) the compound obtained, of formula:

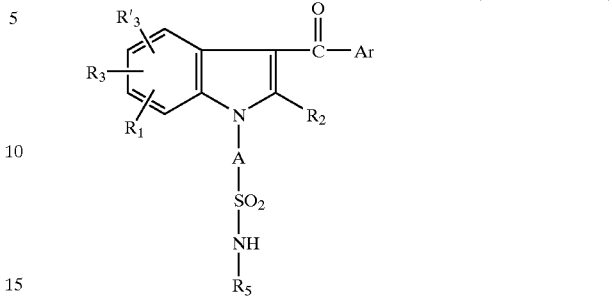

is treated with an alkylating agent in the presence of a base.

15. Process according to claim 10 for preparing a compound of formula (I) in which Y represents an $NR_7SO_2R_4$ group or an $NR_7SO_2NR_5R_6$ group wherein:

b4) the compound of formula:

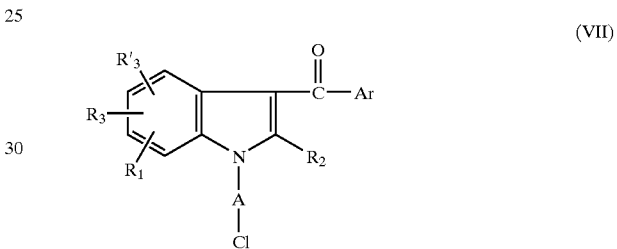

is converted into a compound of formula:

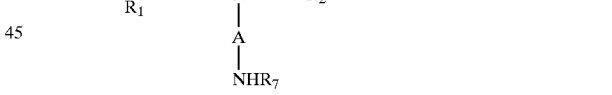

c4) treatment is carried out with a halide of formula $HalSO_2R_4$ or respectively $HalSO_2NR_5R_6$.

16. Process for the preparation of a compound of formula (I) according to claim 1, of its salts and/or solvates wherein:

i) an indole of formula:

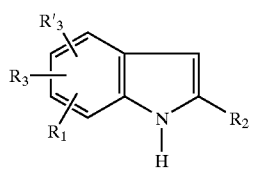

in which $R_1$, $R_2$, $R_3$ and $R'_3$ are as defined for the compound of formula (I), is treated with a halide of formula Hal—A—Y (V) in which —A— and Y are as defined for a compound of formula (I) in claim 1 and Hal represents a halogen atom in the presence of a base;

ii) the compound thus obtained, of formula:

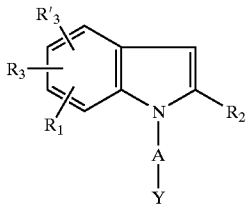

(XII)

is treated with an acid halide of formula ArCOHal (III) and Hal is a halogen atom.

17. Process according to claim 16 wherein:

i1) an indole of formula:

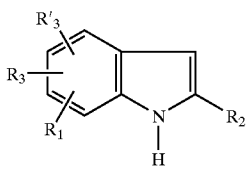

(II)

is treated with a compound of formula Z—A—Cl (VI) and Z represents a hydroxyl group or a halogen atom;

i2) optionally, the compound thus obtained, of formula:

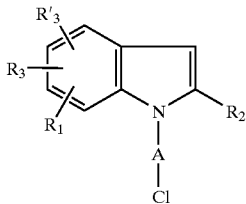

(XIII)

is treated with sodium iodide;

i3) the compound thus obtained in stage i1) or in stage i2), of formula:

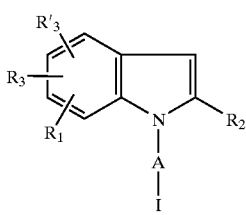

(XIV)

is treated with an anion of formula $Y^-$;

ii) the compound thus obtained, of formula:

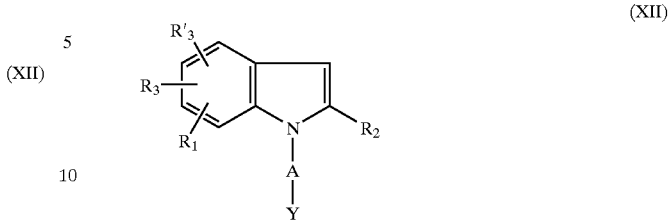

(XII)

is treated with an acid halide of formula ArCOHal (III) and Hal is a halogen atom.

18. Pharmaceutical composition comprising, as active principle, a compound according to claim 1 together with at least one pharmaceutical excipient.

19. Pharmaceutical composition according to claim 18 comprising from 0.1 to 1000 mg of active principle in the form of a dosage unit in which the active principle is mixed with at least one pharmaceutical excipient.

20. A process according to claim 16 wherein Hal represents bromine.

21. Pharmaceutical composition comprising, as active principle, a compound according to claim 2 together with at least one pharmaceutical excipient.

22. Pharmaceutical composition comprising, as active principle, a compound according to claim 3 together with at least one pharmaceutical excipient.

23. Pharmaceutical composition comprising, as active principle, a compound according to claim 4 together with at least one pharmaceutical excipient.

24. Pharmaceutical composition comprising, as active principle, a compound according to claim 5 together with at least one pharmaceutical excipient.

25. Pharmaceutical composition comprising, as active principle, a compound according to claim 6 together with at least one pharmaceutical excipient.

26. Pharmaceutical composition comprising, as active principle, a compound according to claim 7 together with at least one pharmaceutical excipient.

27. Pharmaceutical composition comprising, as active principle, a compound according to claim 8 together with at least one pharmaceutical excipient.

28. Pharmaceutical composition comprising, as active principle, a compound according to claim 9 together with at least one pharmaceutical excipient.

29. N-[3-(6,7-Dichloro-3-[2-fluoro-3-(trifluoromethyl)benzoyl]-2-methyl-1H-indol-1-yl)propyl]methanesulphonamide according to claim 9.

30. Pharmaceutical composition comprising as active principle, a compound according to claim 29 together with at least one pharmaceutical excipient.

* * * * *